United States Patent
Pope et al.

(10) Patent No.: US 11,629,318 B2
(45) Date of Patent: Apr. 18, 2023

(54) METHODS FOR PRODUCING MATURE ADIPOCYTES AND METHODS OF USE THEREOF

(71) Applicant: President and Fellows of Harvard College, Cambridge, MA (US)

(72) Inventors: Benjamin D. Pope, Watertown, MA (US); Kevin Kit Parker, Cambridge, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 172 days.

(21) Appl. No.: 16/757,133

(22) PCT Filed: Oct. 19, 2018

(86) PCT No.: PCT/US2018/056649
§ 371 (c)(1),
(2) Date: Apr. 17, 2020

(87) PCT Pub. No.: WO2019/079681
PCT Pub. Date: Apr. 25, 2019

(65) Prior Publication Data
US 2020/0248116 A1    Aug. 6, 2020

Related U.S. Application Data

(60) Provisional application No. 62/574,801, filed on Oct. 20, 2017.

(51) Int. Cl.
| | | |
|---|---|---|
| *C12M 3/00* | (2006.01) | |
| *A61K 35/28* | (2015.01) | |
| *C12M 1/00* | (2006.01) | |
| *C12M 1/12* | (2006.01) | |
| *C12N 5/077* | (2010.01) | |

(52) U.S. Cl.
CPC ............ *C12M 21/08* (2013.01); *A61K 35/28* (2013.01); *C12M 23/20* (2013.01); *C12M 25/00* (2013.01); *C12N 5/0653* (2013.01); *C12N 2533/30* (2013.01); *C12N 2533/90* (2013.01); *C12N 2535/00* (2013.01)

(58) Field of Classification Search
None
See application file for complete search history.

(56) References Cited

U.S. PATENT DOCUMENTS

| | | |
|---|---|---|
| 6,713,772 B2 | 3/2004 | Goodman et al. |
| 6,821,107 B1 | 11/2004 | Hara et al. |
| 6,829,035 B2 | 12/2004 | Yogev |
| 7,043,292 B2 | 5/2006 | Tarjan et al. |
| 7,115,377 B2 | 10/2006 | Yao et al. |
| 7,122,307 B2 | 10/2006 | Rosen et al. |
| 8,492,150 B2 | 7/2013 | Parker et al. |
| 8,748,181 B2 | 6/2014 | Kuo et al. |
| 8,999,378 B2 | 4/2015 | Parker et al. |
| 9,012,172 B2 | 4/2015 | Parker et al. |
| 9,068,168 B2 | 6/2015 | Feinberg et al. |
| 9,383,350 B2 | 7/2016 | Parker et al. |
| 9,669,141 B2 | 6/2017 | Parker et al. |
| 9,719,982 B2 | 8/2017 | Parker et al. |
| 9,857,356 B2 | 1/2018 | Parker et al. |
| 2001/0023073 A1 | 9/2001 | Bhatia et al. |
| 2002/0137715 A1 | 9/2002 | Mauviel |
| 2003/0059103 A1 | 3/2003 | Shiomi et al. |
| 2003/0059537 A1 | 3/2003 | Chilkoti et al. |
| 2003/0134331 A1 | 7/2003 | Marks et al. |
| 2004/0009566 A1 | 1/2004 | Okano et al. |
| 2004/0048239 A1 | 3/2004 | Farinas et al. |
| 2004/0078090 A1 | 4/2004 | Binette et al. |
| 2004/0101819 A1 | 5/2004 | Montemagno et al. |
| 2005/0048414 A1 | 3/2005 | Harnack et al. |
| 2005/0080402 A1 | 4/2005 | Santamore et al. |
| 2005/0085847 A1 | 4/2005 | Galdonik et al. |
| 2005/0202569 A1 | 9/2005 | Sakaino et al. |
| 2005/0287557 A1 | 12/2005 | Efendic |
| 2006/0003439 A1 | 1/2006 | Ismagilov et al. |
| 2006/0029922 A1 | 2/2006 | Van Eelen et al. |
| 2006/0071286 A1 | 4/2006 | Axelrod et al. |
| 2006/0134692 A1 | 6/2006 | Emmert-Buck et al. |
| 2006/0136182 A1 | 6/2006 | Vacant et al. |

(Continued)

FOREIGN PATENT DOCUMENTS

| | | |
|---|---|---|
| EP | 0387975 A1 | 9/1990 |
| EP | 1302535 A1 | 4/2003 |

(Continued)

OTHER PUBLICATIONS

Patrick, "Adipose Tissue Engineering: The future of Breast and Soft Tissue Reconstruction Following Tumor Resection" (2000) Sem Surg Oncol, bol. 19: 302-311. (Year: 2000).*

Kang et al. "Adipose Tissue Model Using Three-Dimensional Cultivation of Preadipocytes Seeded onto Fibrous Polymer Scaffolds" (2005), vol. 11: 458-468. (Year: 2005).*

Alford, P.W., et al., "Biohybrid Thin Films for Measuring Contractility in Engineered Cardiovascular Muscle." Biomaterials. 2010, 31: 3613-3621.

Yang et al., "Fabrication of well-defined PLGA scaffolds using novel microembossing and carbon dioxide bonding", Biomaterials, 2005, vol. 25., pp. 2585-2594.

(Continued)

*Primary Examiner* — Teresa E Knight

(74) *Attorney, Agent, or Firm* — McCarter & English, LLP; Maria Laccotripe Zacharakis; Anita M. Bowles

(57) ABSTRACT

The present invention provides methods and systems which accommodate 3-dimensional adipocyte expansion to produce, e.g., mature adipocytes and synthetic adipose tissue with cellular properties of mature adult organisms, including cell size and cytoarchitecture, and the use of such methods and systems for, e.g., in vitro drug screening and/or toxicity assays, disease modeling, and therapeutic applications.

17 Claims, 11 Drawing Sheets

(56) References Cited

U.S. PATENT DOCUMENTS

| | | |
|---|---|---|
| 2006/0153816 A1 | 7/2006 | Brown et al. |
| 2006/0253192 A1 | 11/2006 | Atala |
| 2007/0053996 A1 | 3/2007 | Boyden et al. |
| 2007/0060815 A1 | 3/2007 | Martin et al. |
| 2007/0164641 A1 | 7/2007 | Pelrine et al. |
| 2007/0190646 A1 | 8/2007 | Engler et al. |
| 2007/0197857 A1 | 8/2007 | Palmer |
| 2008/0031818 A1 | 2/2008 | Bush |
| 2008/0085265 A1 | 4/2008 | Schneider et al. |
| 2008/0118985 A1 | 5/2008 | Torres et al. |
| 2009/0023773 A1 | 1/2009 | Vohra et al. |
| 2009/0054954 A1 | 2/2009 | Foley et al. |
| 2009/0061031 A1 | 3/2009 | Lee-Huang et al. |
| 2009/0076530 A1 | 3/2009 | Fukutomi et al. |
| 2009/0098628 A1 | 4/2009 | Ramasubramanian |
| 2009/0317852 A1 | 12/2009 | Parker et al. |
| 2010/0041972 A1 | 2/2010 | Mason |
| 2010/0196432 A1 | 8/2010 | Feinberg et al. |
| 2010/0305460 A1 | 12/2010 | Pinter et al. |
| 2010/0330644 A1 | 12/2010 | Feinberg et al. |
| 2011/0041935 A1 | 2/2011 | Zhou et al. |
| 2011/0189719 A1 | 8/2011 | Kuo et al. |
| 2011/0250585 A1 | 10/2011 | Ingber et al. |
| 2012/0029416 A1 | 2/2012 | Parker et al. |
| 2012/0134570 A1 | 5/2012 | Trumbull et al. |
| 2012/0135448 A1 | 5/2012 | Parker et al. |
| 2012/0142556 A1 | 6/2012 | Parker et al. |
| 2013/0046134 A1 | 2/2013 | Parker et al. |
| 2013/0053625 A1 | 2/2013 | Merc Vives |
| 2013/0234013 A1 | 9/2013 | Patterson et al. |
| 2013/0289675 A1 | 10/2013 | Deisseroth et al. |
| 2013/0312638 A1 | 11/2013 | Parker et al. |
| 2013/0330378 A1 | 12/2013 | Parker et al. |
| 2014/0080206 A1 | 3/2014 | Dahan et al. |
| 2014/0151224 A1 | 6/2014 | Glezer et al. |
| 2014/0235826 A1 | 8/2014 | Deisseroth et al. |
| 2014/0236267 A1 | 8/2014 | Parker |
| 2014/0311912 A1 | 10/2014 | Shih et al. |
| 2014/0322515 A1 | 10/2014 | Parker et al. |
| 2014/0342394 A1 | 11/2014 | Parker et al. |
| 2014/0370111 A1 | 12/2014 | Boyan et al. |
| 2014/0377320 A1 | 12/2014 | Pietramaggiori et al. |
| 2015/0004077 A1 | 1/2015 | Wikswo et al. |
| 2015/0182679 A1 | 7/2015 | Parker et al. |
| 2015/0219622 A1 | 8/2015 | Hickman |
| 2015/0253307 A1 | 9/2015 | Parker et al. |
| 2015/0354094 A1 | 12/2015 | Parker et al. |
| 2016/0003806 A1 | 1/2016 | Parker et al. |
| 2016/0331528 A1 | 11/2016 | Parker et al. |
| 2017/0016875 A1 | 1/2017 | Parker et al. |
| 2018/0172672 A1 | 6/2018 | Parker et al. |
| 2018/0209957 A1 | 7/2018 | Parker et al. |
| 2018/0327702 A1 | 11/2018 | Gannon et al. |
| 2018/0357927 A1 | 12/2018 | Parker et al. |
| 2018/0372725 A1 | 12/2018 | Parker et al. |

FOREIGN PATENT DOCUMENTS

| | | |
|---|---|---|
| WO | WO-2004/014212 A2 | 2/2004 |
| WO | WO-2006/068972 A2 | 6/2006 |
| WO | WO-2008/045506 A2 | 4/2008 |
| WO | WO-2008/051265 A2 | 5/2008 |
| WO | WO-201 0/127280 A1 | 11/2010 |
| WO | WO-2010/127280 A1 | 11/2010 |
| WO | WO-2010/132636 A1 | 11/2010 |
| WO | WO-2011/102991 A1 | 8/2011 |
| WO | WO-2012/006320 A1 | 1/2012 |
| WO | WO-2012/048242 A1 | 4/2012 |
| WO | WO-2012/131360 A2 | 10/2012 |
| WO | WO-2013/086512 A2 | 6/2013 |
| WO | WO-2013/115896 A2 | 8/2013 |
| WO | WO-2016/007879 A1 | 1/2016 |
| WO | WO-2016/045813 A1 | 3/2016 |
| WO | WO-2016/069142 A2 | 5/2016 |
| WO | WO-2016/191179 A1 | 12/2016 |
| WO | WO-2017/027390 A1 | 2/2017 |
| WO | WO-2017/087759 A1 | 5/2017 |
| WO | WO-2018/027105 A1 | 2/2018 |
| WO | WO-2019079714 A1 | 4/2019 |

OTHER PUBLICATIONS

Bray et al., "Sarcomere Alignment is Regulated by Myocyte Shape" *Cell Motility and the Cytoskeleton*, Aug. 2008, 65(8), pp. 641-651.

Parker et al., "Extracellular matrix, mechanotransduction and structural hierarchies in heart tissue engineering." Phil Trans R. Soc B, Epub, Jun. 22, 2007, vol. 362, pp. 1267-1279.

Park et al., "Real-Time Measurement of the Contractile Forces of Self-Organized Cardiomyocytes on Hybrid Biopolymer Microcantilevers," Anal. Chem. Oct. 2005, 77:6571-6580.

Mao et al., "Capillary isoelectric focusing with whole colomn imaging detection for analysis of proteins and peptides," J. Biochem. Biophys. Methods, Feb. 1999, 39:93-110.

International Search Report from PCT/US2011/043027 dated Jul. 6, 2011.

Badrossamay, M.R. et al. "Nanofiber assembly by rotary jet-spinning." Nano Letters, May 2010;10(6):2257-2261.

Vandenburgh et al., "Drug-Screening Platform Based on the Contractility of Tissue-Engineered Muscle", Muscle Nerve 37:438-447, 2008.

Kim et al., "Biohybrid Microsystems Actuated by Cardiomyocytes: Microcantilever, Microrobot, and Micropump", Proceedings—IEEE International Conference on Robotics and Automation. 880-885. (2008).

Shimizu et al."Microfluidic devices for construction of contractile skeletal muscle microtissues" Journal of Bioscience and Bioengineering, vol. 119, Issue 2, Feb. 2015, pp. 212-216.

Luo, Y and Zare, RN, "Perforated membrane method for fabricating three-dimensional polydimethylsiloxane microfluidic devices", Lab Chip, 2008, 8, 1688-1694. doi: 10.1039/b807751g.

Xi et al., "Development of a Self-Assembled Muscle-Powered Piezoelectric Microgenerator", NSTI-Nanotech, 2004, vol. 1, pp. 3-6.

International Search Report from PCT/US2013/060823, dated Apr. 15, 2014.

International Search Report and Written Opinion from PCT/US2015/016395, dated Jan. 6, 2016 pp. 1-16.

International Preliminary Report on Patentability for Application No. PCT/US2015/051818, dated Apr. 6, 2017. 8 pages.

International Search Report and Written Opinion from PCT/US2015/051818 dated Jun. 2, 2016.

Bol, M., et al. "Computational modeling of muscular thin films for cardiac repair." Computational Mechanics. Sep. 13, 2009;43(4):535-44.

Feinberg, A.W., et al. "Muscular thin films for building actuators and powering devices." Science. Sep. 7, 2007;317(5843):1366-70.

Geisse, N.A., et al. "Micropatterning Approaches for Cardiac Biology." In: Khademhosseini A, Toner M, Borenstein JT, Takayama S, editors. Micro- and Nanoengineering of the Cell Microenvironment: Technologies and Applications. Boston: Artech House;2008, p. 341-357.

Nawroth et al., "A Tissue-engineered jellyfish with biomimetic propulsion", Nature Biotechnology, 2012, vol. 30, No. 8, pp. 792-800.

Johnsrude et al., "Mechanical Properties of the Myotomal Muscoskeletal System of Rainbow Trout, Salmo Gairdneri", Journal of Exp. Biol., 1985, vol. 119, pp. 71-83.

Parker, K.K. ,et al. "Myofibrillar architecture in engineered cardiac myocytes. <http://diseasebiophysics.seas.harvard.edu/pdfs/017-2008AugC- ircRes.pdf>" Circ Res. Aug. 15, 2008;103(4):340-2.

Hu, S et al "Mechanical Anisotropy of Adherent Cells Probed by a Three-dimensional Magnetic Twisting Device" Am J Physiol Cell Physiol, 2004, 287(5), pp. C1184-C1191.

Anversa et al., "Morphometry of exercise-induced right ventricular hypertrophy in the rat." (1983) Circ Res 52:57-64.

Anversa et al., "Myocyte Cell Loss and Myocyte Hypertrophy in the Aging Rat Heart" (1986) J Amer Coll Cardiol 7:1140-9.

(56) References Cited

OTHER PUBLICATIONS

Atherton et al., "Assembly and remodeling of Myofibrils and Intercalated Discs in Cultured Neonatal Rat Heart Cells" (1986) J Cell Sci 86:233-48.
Balaban et al., "Force and focal adhesion assembly: a close relationship studied using elastic micropatterned substrates" (2001) Nat Cell Biol 3:466.
Beauchamp et al., "Relative Contributions of Connexins 40 and 43 to Atrial Impulse Propagation in Synthetic Strands of Neonatal and Fetal Murine Cardiomyocytes" (2006) Circ Res 99:1216-24.
Bershadsky et al., "Adhesion-Dependent Cell Mechanosensitivity" (2003) Annu Rev Cell Dev Biol 19:677.
Brancaccio et al., "Integrin signalling: The tug-of-war in heart hypertrophy" (2006) Cardiovasc Res 70:422-33.
Brower et al., "The relationship between myocardial extracellular matrix remodeling and ventricular function" (2006) Eur J Cardiothorac Surg 30:604-10.
Bursac et al., "Multiarm spirals in a two-dimensional cardiac substrate" (2004) Proc Natl Acad Sci USA 101:15530-4.
Camelliti et al., "Microstructured Cocuhures of Cardiac Myocylesand Fibroblasts: A Two Dimensional in Vitro Model of Cardiac Tissue" (2005) Microsc Microanal 11:249-59.
Chen et al., "Geometric Control of Cell Life and Death" (1997) Science 276:1425-8.
Chen et al., "Cell shape provides global control of focal adhesion assembly" (2003) Biochem Biophys Res Commun 307:355-61.
Chen et al., "Regional ventricular wall thickening reflects changes in cardiac fiber and sheet structure during contraction: quantification with diffusion tensor MRI" (2005) Am J. Physio.-Heart Circul Physiol 289:H1898-H1907.
Chrzanowska-Wodnicka et al., "Rho-Stimulated Contractility Drives the Formation of Stress Fibers and Focal adhesions" (1996) J Cell Biol 133:1403.
Dabiri et al., "Myofibrillogenesis visualized in living embryonic cardiomyocytes" (1997) Proc Natl Aced Sci USA 94:9493.
Danowski et al., "Costameres are Sites of Force Transmission to the Substratum in Adult Rat Cardiomyoctes" (1992) J Cell Biol 118:1411-20.
Dembo et al., "Stresses at the Cell-to-Substrate Interface during Locomotion of Fibroblasts" (1999) Biophys J 76:2307.
Ding et al., "Left Ventricular Hypertrophy in Ascending Aortic Stenosis Mice : Anoikis and the Progression to Early Failure" (2000) Circulation 101:2854-62.
Dlugosz et al. "The Relationship between Stress Riber-Like Structures and Nascent Myofibrils in Cultured Cardiac Myocytes" (1984) J Cell Biol 99:2268.
Du et al., "Myofibrillogenesis in the first cardiomyocytes formed from isolated quail precardiac mesoderm" (2003) Dev Biol 257:382.
Ehler et al., "Myofibrillogenesis in the developing chicken heart: assembly of Z-disk, M-line and the thick filaments" (1999) J Cell Sci 112 (Pt 10):1529.
Ezzell et al., "Vinculin Promotes Cell Spreading by Mechanically Coupling Integrins to the Cytoskeleton" (1997) Exp Cell Res 231:14-26.
Furuta et al., "Pulsatile Cardiac Tissue Grafts Using a Novel Three-Dimensional Cell Sheet Manipulation Technique Functionally Integrates With the Host Heart, in Vivo" (2006) Circ Res 98:705-12.
Galbraith et al., "The relationship between force and focal complex development" (2002) J Cell Biol 159:695.
Gerdes et al. (1988) Lab Invest 59:857-61.
Gerdes et al. (1992) Circulation 86:426-30.
Gopalan et al., "Anisotropic Stretch-induced Hypertrophy in Neonatal Ventricular Myocytes Micro patterned on Deformable Elastomers" (2003) Biotechnol Bioeng 81:578-87.
Harrington, et al., "Direct measurement of transmural laminar architecture in the anterolateral wall of the ovine left ventricle: new implications for wall thickening mechanics" (2005) Am J Physiol-Heart Circul Physiol 288:H1324-H1330.
Hilenski et al. "Myofibrillar and cytoskeletal assembly in neonatal rat cardiac myocytes cultured on laminin and collagen" (1991) Cell and Tissue Research 264:577-87.
Holtzer et al., "Independent Assembly of 1.6 /an Long Bipolar MHCFilaments and I-Z-I Bodies" (1997) Cell Struct Funct 22:83.
Huang et al. , "Control of Cyclin D1, p27Kip1, and Cell Cycle Progression in Human Capillary Endothelial Cells by Cell Shape and Cytoskeletal Tension" (1998) Mol Biol Cell 9:3179-93.
Ingber, "Integrins as Mechanochemical transducers" (1991) Current Opinion in Cell Biology 3:841-8.
Jiang et al., "Directing cell migration with asymmetric micropatterns" (2005) Proc Natl Acad Sci USA 102:975-8.
Komuro et al., "Control of Cardiac Gene Expression by Mechanical Stress" (1993) Annu Rev Physiol 55:55-75.
Legrice et al. "Laminar structure of the heart: ventricular myocyte arrangement and connective tissue architecture in the dog" (1995) Am J Physiol-Heart Circul Physiol 38:H571-H582.
Lehnert et al., "Cell behaviour on micro patterned substrata: limits of extracellular matrix geometry for spreading and adhesion" (2004) J Cell Sci 117:41-52.
Lin et al., "Polygons and Adhesions Plaques and the Disassembly and Assembly of Myofibrils in Cardiac Myocytes" (1989) J Cell Biol 108:2355-67.
Lu et al., The Vinculin/Sarcomeric-.alpha.-Actinin/.alpha.-Actin Nexus in Cultured Cardiac Myocytes: (1992) J Cell Biol 117:1007-22.
Mansour et al., "Restoration of Resting Sarcomere Length After Uniaxial Static Strain Is Regulated by Protein Kinase C.sub.—and Focal Adhesion Kinase" (2004) Circ Res 94:642-9.
Maxwell et al., "The integration of tissue structure and nuclear Function" (2001) Biochemistry and Cell Biology 79:267-74.
McKenna et al., "Formation and Alignment of Z Lines in Living Chick Myotubes Microinjected with Rhodamine-Labeled Alpha-Actinin" (1986) J Cell Biol 103:2163.
O'Neill et al., "Narrow linear strips of adhesive substratum are powerful inducers of both growth and total focal contact area" (1990) J Cell Sci 95:577-86.
Novak et al., "Cooperativity between Cell Contractility and Adhesion" (2004) Phys Rev Lett 93, 268109.
Onodera et al., "Maladaptive Remodeling of Cardiac Myocyte Shape Begins Long Before Failure in Hypertension" (1998) Hypertension 32:753-7.
Parker et al., "Directional control of lamellipodia extension by constraining cell shape and orienting cell tractional forces" (2002) Faseb J 16:1195.
Pelham et al., "Cell locomotion and focal adhesions are regulated by substrate flexibility" (1997) Proc Natl Aced Sci USA 94:1366.
Rhee et al., "The Premyofibril: Evidence for its Role in Myofi brillogenesis"(1994) Cell Motil Cytoskeleton 28:1.
Rohr et al., "Patterned growth of neonatal rat heart cells in culture. Morphological and electrophysiological characterization" (1991) Circ Res 68:114-30.
Rothen-Rutishauser et al., "Different Behaviour of the Non-sarcomeric Cytoskeleton in Neonatal and Adult Rat Cardiomyocytes" (1998) J Mol Cell Cardiol 30:19-31.
Russell et al., "Form follows function: how muscle shape is regulated by work" (2000) J Appl Physiol 88, 1127.
Samarel, "Costameres, focal adhesions, and cardiomyocyte mechanotransduction" (2006) Am J Physiol Heart Circ Physiol 289:H2291-H2301.
Sands et al., "Automated Imaging of Extended Tissue Volumes Using Confocal Microscopy"Microscopy Research and Technique 67:227-239 (2005).
Sanger et al., "Myofibrillogenesis in Living Cells Microinjected with Fluorescently Labels Alpha-Actinin" (1986) J Cell Biol 102:2053.
Siegrist et al., "Extrinsic cues orient the cell division axis in *Drosophila* embryonic neuroblasts" (2006) Development 133:529.
Simpson et al., "Mechanical regulation of cardiac myocyte protein turnover and myofibrillar structure" (1996) Am J Physiol Cell Physiol 270:C1075-C1087.
Simpson et al. "Regulation of Cardiac Myocyte Protein Turnover and Myofibrillar Structure in Vitro by Specific Directions of Stretch" (1999) Circ Res 85:e59-e69.

(56) References Cited

OTHER PUBLICATIONS

Singhvi et al., "Engineering Cell Shape and Function" (1994) Science 264:696-8.
Smilenov et al., "Focal Adhesion Motility Revealed in Stationary Fibroblasts" (1999) Science 286:1172.
Smith et al., "Regional Myocyte Size in Compensated Right Ventricular Hypertrophy in the Ferret" (1985) 17:1005-11.
Tan et al., "Simple Approach to Micropattern Cells on Common Culture Substrates by Tuning Substrate Wettability" (2004) Tissue Eng 10:865.
Thery et al., "Cell Distribution of Stress Fibres in Response to the Geometry of the Adhesive Environment" (2006) Cell Motil Cytoskeleton 63:341.
Tokuyasu et al., "Intermediate Filaments in Skeletal and Cardiac Muscle Tissue in Embryonic and Adult Chicken .sup.a"(1985) Ann NY Acad Sci 455:200-12.
Tokuyasu, "Immunocytochemical Studies of Cardiac Myofibrillogenesis in Early Chick Embryos. III. Generation of Fasciae Adherentes and Costamers"(1989) J Cell Biol 108:43-53.
Torsoni et al., "Focal Adhesion Kinase is Activated and Mediates the Early Hypertrophic Response to Stretch in Cardiac Myocytes" (2003) Circ Res 93:140.
Young et al., "Extended confocal microscopy of myocardial laminae and collagen network" Journal of Microscopy, vol. 192, Pt 2, Nov. 1998, pp. 139-150.
Wang, "Reorganization of Actin Filament Bundles in Living Fibroblasts", (1984) J Cell Biol 99:1478.
Wang et al., "Micropatterning Tractional Forces in Living Cells" (2002) Cell Motil Cytoskeleton 52:97.
Weiss et al., "Shape and Movement of Mesenchyme Cells as Functions of the Physical Structure of the Medium Contributions to a Quantitative Morphology" (1952) Proc Natl Acad Sci USA 38:264-80.
Zamir et al., "Dynamics and segregation of cell-matrix adhesions in cultured fibroblasts" (2000) Nat Cell Biol 2:191.
Laanilainen, Eeva "Soft Lithography for Surface Micropatterning", Thesis, Helsinki Univ. of Tech., Jun. 29, 2006, 94 pp.
McDonald, JC and Whitesides, GM "Poly(dimethylsiloxane) as a Material for Fabricating Microfluidic Devices" Acc. Chem. Res., Jul. 2002, 35(7), pp. 491-499.
Narasimhan, SV; Goodwin, RL; Borg, TK; Dawson, DM; Gao, BZ "Multiple Beam Laser Cell Micropatterning System" Optical Trapping and Optical Micromanipulation, Proc. SPIE., Oct. 18, 2004, 5514, pp. 437-445.
Grosberg et al., "Ensembles of engineered cardiac tissues for physiological and pharmacological study: Heart on a chip." Lab Chip, 2011, vol. 11, p. 4165.
Spring, "Electronic Imaging in Neuroscience," Curr. Protoc. Neurosci. 2002, 2.4.1-2.4.9.
Pilarek et al, "Biological cardio-micro-pumps for microbioreactors and analytical micro-systems", (Aug. 2011), Sensors and Actuators B: Chemical, vol. 156, Issue 2, pp. 517-526.
International Search Report and Written Opinion from PCT/US2016/062693, dated Apr. 14, 2017.
Neubauer Stem Cell-based Adipose Tissue Engineering,Universitat Regensburg, Nov. 2004. [Retrieved on Mar. 22, 2022], Retrieved from the Internet: ,https://epub.uni-regensburg.de/10269/. pp. 1-50.
International Search Report and Written Opinion from PCT/US2018/056649, dated Jan. 4, 2019.

\* cited by examiner

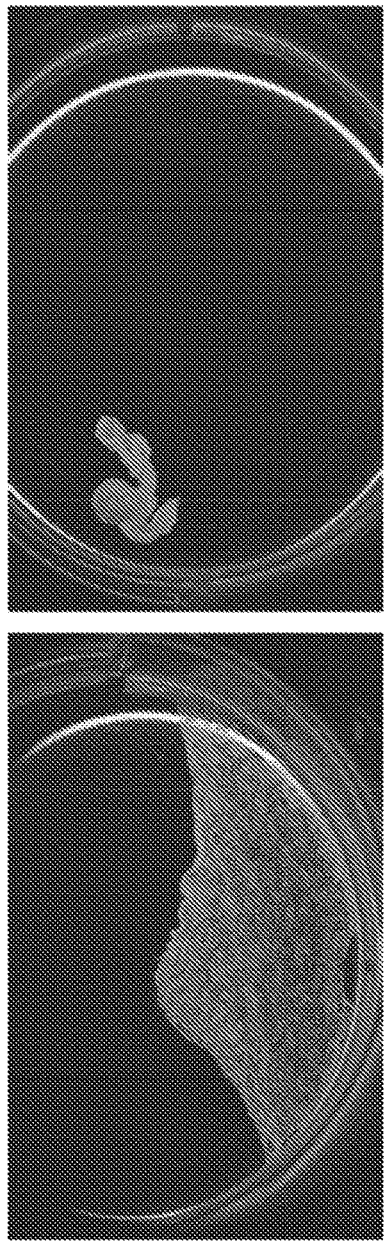
FIG. 1A
FIG. 1B
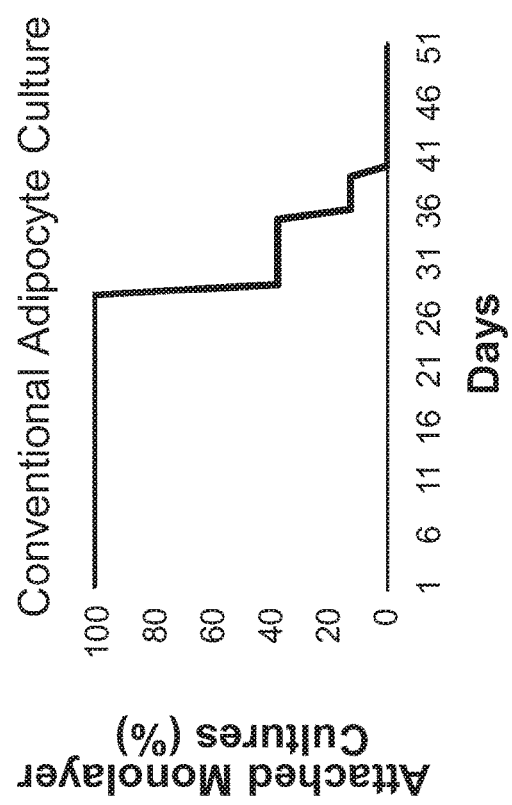
FIG. 1C

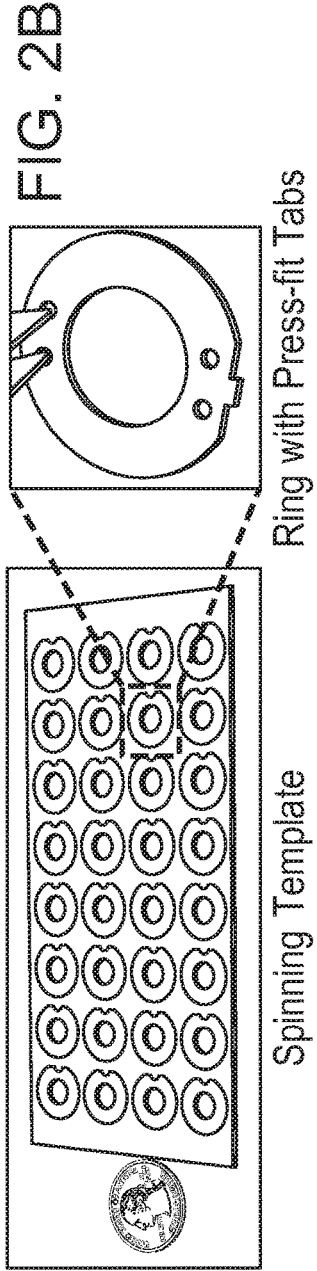
FIG. 2A
FIG. 2B
Ring with Press-fit Tabs
Spinning Template
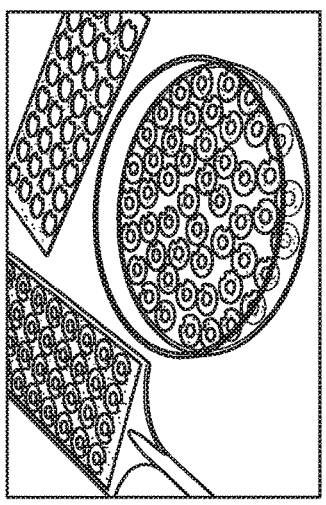
FIG. 2D
Batch Fabrication
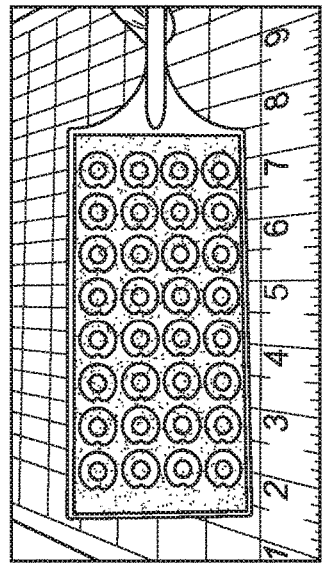
FIG. 2C
Template on Collection Mandrel
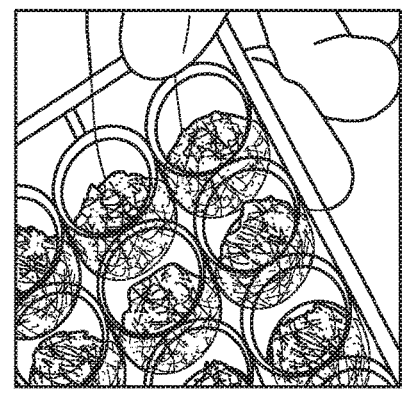
FIG. 2E

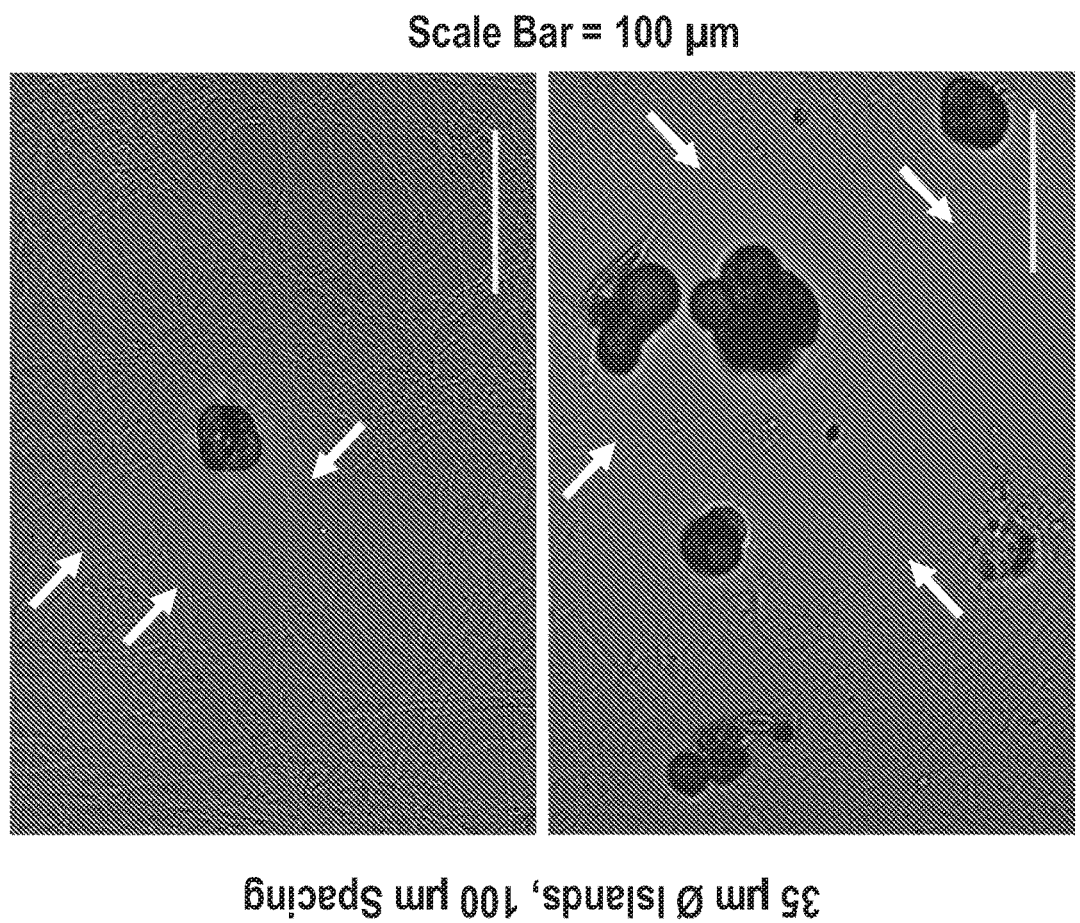

METHODS FOR PRODUCING MATURE ADIPOCYTES AND METHODS OF USE THEREOF

RELATED APPLICATIONS

This application is a U.S. national stage filing, under 35 U.S.C. § 371(c), of International Application No. PCT/US2018/056649, filed on Oct. 19, 2018, which claims the benefit of priority to U.S. Provisional Application No. 62/574,801, filed on Oct. 20, 2017, the entire contents of each of which are incorporated herein by reference.

GOVERNMENT SUPPORT

The invention was made with government support under HL107440 and DK104165 awarded by National Institutes of Health (NIH). The government has certain rights in this invention.

BACKGROUND OF THE INVENTION

Adipose tissue is present in vertebrate organisms, performing vital functions including energy storage and metabolism, hormone secretion, mechanical shock absorption, and insulation. Large (up to 290-μm diameter) spherical adipocytes make up the tissue and are typically arranged in an imperfect hexagonal packing architecture resembling honeycomb. The cytoarchitecture, cell size, and lipid composition of adipose tissue contribute to the taste and texture of meat and the shape, stiffness, and structural integrity of body parts. As such, adipose tissue is an important element of tissue engineered food and fat grafting for reconstructive surgery or cosmetic enhancement. Moreover, excess (or inadequate) adipose tissue is often pathogenic and methods to prevent obesity or eliminate its pathogenic consequences are of great interest and value.

In vivo, adipocyte hypertrophy is a primary mode of weight gain in which an adipocyte expands up to several thousand-fold in size. Conventional adipocyte culture is performed on generic gelatin-coated 2-dimensional (2-D) polystyrene tissue culture dishes with a limited lifespan (~1 month) and is made up of randomly organized cells with variable differentiation status (~40% adipocytes) and immature cell size (2 orders of magnitude below mature tissue). However, as soon as lipid accumulation occurs in vitro and the cells are approximately 20 microns in diameter, cell buoyancy increases causing adipocytes to detach from conventional planar culture surfaces, fold-up and lyse well before reaching cell sizes observed in adult humans (Table 1, below; reproduced from Pope et al. (2016) *Trends in Cell Biology* doi: 10.1016/j.tcb.2016.05.005). Therefore, the current methods for culturing adipocytes do not permit the adipocytes to achieve or maintain in vivo structure or function. At most, adipocytes cultured on gelatin-coated culture dishes achieve a size about 8 times less than mature cells in vivo, e.g., adult human adipocytes, before floating off of the culture surface. Therefore, these cultured adipocytes do not function as they would in an in vivo environment.

TABLE 1

Adipocyte Sizes in Developing and Adult Humans versus in vitro Culture

| Cell Size | Subcutaneous and Visceral Fat | | | Subcutaneous Fat | | Visceral Fat | | 2D Culture |
|---|---|---|---|---|---|---|---|---|
| | Fetus[a] | Neonate | Infant[b] | Lean | Obese | Lean | Obese | |
| Diameter range (μm) | 40-50 | 50-80 | 90-130 | 50-130 | 90-270 | 45-110 | 90-200 | 20-60 |
| Mean cell volume (μm$^3$) | 48 000 | 144 000 | 697 000 | 382 000 | 3 054 000 | 244 000 | 1 596 000 | 65 000 |

[a]25-30 weeks gestation.
[b]1-3 months postpartum.

Although several platforms have been developed that support adipogenesis, none of these platforms overcome the limitations that 2-dimensional cultures impose on adipocyte size and enable the production of mature adipocytes.

Accordingly, there is a need in the art for methods and systems that support adipocyte differentiation and growth to enable the production of mature human adipocytes in vitro.

SUMMARY OF THE INVENTION

The present invention is based, at least in part, on the discovery of methods and systems that support adipocyte differentiation and growth of mesenchymal progenitor cells and enable adipocyte hypertrophy (an increase in the size of the cells) so that mature human adipocytes are produced in vitro.

In particular, methods and systems which accommodate 3-dimensional (3-D) adipocyte expansion and which include protein micropatterning to position and coax differentiation of pre-adipocytes with a nanofibrous network that covers and restrains the micropatterned adipocytes during maturation and hypertrophic growth have been discovered. The network extends the lifespan of adipocyte cultures from one to over six months as well as increased average cell size over 50-fold relative to conventional culture (e.g., 2-D gelatin-coated plate culture). In addition, it has been discovered that the spacing between adipocytes in the micropattern controls the rate of hypertrophy independent of time in culture and, thus, this parameter can be used to tune adipocyte size in the islands. For example, islands spaced 50 um apart are nearly confluent at seeding and produce cell sizes similar to 2D culture, while islands that are spaced 200 um apart can be cultured to 200 um diameter.

Accordingly, in one aspect, the present invention provides a method for producing mature adipocytes in vitro. The method includes providing a support having a first surface including a pattern of islands, each island having a length, width, or diameter in a range of about 10 μm to about 100 μm, and a center to center spacing between adjacent islands being in a range of about 20 μm to about 300 μm, each island comprising one or more layers of an extracellular matrix protein; seeding the pattern of islands with a plurality of mesenchymal progenitor cells and culturing the mesenchymal progenitor cells under conditions that induce adipogenesis of at least one of the mesenchymal progenitor cells, thereby producing adipocyte islands; disposing a fiber layer over the first surface of the support and over the adipocytes on the islands, each fiber layer comprising a plurality of polymer fibers each having a diameter in a range of about 100 nm to about 1 µm; and culturing the adipocytes with the fiber layer over the adipocytes under suitable conditions until at least one of the adipocytes grows to a diameter of between about 30 µm and about 300 µm, thereby generating mature adipocytes in vitro.

The adipocytes may be cultured with the fiber layer over the adipocytes until at least some of the adipocytes grow to a diameter of between about 50 µm and about 280 µm; a diameter of between about 80 µm and about 280 µm; a diameter of between about 90 µm and about 280 µm; or a diameter of between about 130 µm and about 280 µm.

Each island may have a length, width, or diameter in a range of about 10 µm to about 60 µm; about 20 µm to about 50 µm; or about 20 µm to about 40 µm.

Each of the polymer fibers may independently comprise greater than about 50 wt % polycaprolactone (PCL). Each of the polymer fibers may independently further comprise about 5 to about 49 wt % gelatin.

Each of the polymer fibers may independently have a diameter in a range of about 400 nm to about 800 nm; or about 420 to about 620 nm.

In one aspect, the present invention provides a plurality of mature adipocytes produced according the methods of the invention.

In another aspect, the present invention provides a tissue-engineered food product comprising a plurality of the mature adipocytes produced according to the methods of the invention.

In one aspect, the present invention provides a method for identifying a compound that modulates adipocyte viability, adipocyte hypertrophy, and/or adipocyte function. The method includes providing a support having a first surface including a pattern of islands, each island having a length, width, or diameter in a range of about 10 µm to about 100 µm, and a center to center spacing between adjacent islands being in a range of about 20 µm to about 300 µm, each island comprising one or more layers of an extracellular matrix protein; seeding the pattern of islands with a plurality of mesenchymal progenitor cells and culturing the mesenchymal progenitor cells under conditions that induce adipogenesis of at least one of the mesenchymal progenitor cells, thereby producing adipocyte islands; contacting the adipocyte islands with a test compound; disposing a fiber layer over the first surface of the support and over the adipocytes on the islands, each fiber layer comprising a plurality of polymer fibers each having a diameter in a range of about 100 nm to about 1 µm; culturing the adipocytes with the fiber layer over the adipocytes under suitable conditions until at least one of the adipocytes grows to a diameter of between about 30 µm and about 300 µm; and determining the effect of the test compound on adipocyte viability, adipocyte hypertrophy, and/or adipocyte function in the presence and absence of the test compound, wherein a modulation of adipocyte viability, adipocyte hypertrophy, and/or adipocyte function in the presence of said test compound as compared to adipocyte viability, adipocyte hypertrophy, and/or adipocyte function in the absence of said test compound indicates that said test compound modulates adipocyte viability, adipocyte hypertrophy, and/or adipocyte function, thereby identifying a compound that modulates adipocyte viability, adipocyte hypertrophy, and/or adipocyte function, e.g., energy storage and metabolism, hormone secretion, mechanical shock absorption, and insulation.

In another aspect, the present invention provides a method for identifying a compound that modulates adipocyte viability, adipocyte hypertrophy, and/or adipocyte function. The method includes providing a support having a first surface including a pattern of islands, each island having a length, width, or diameter in a range of about 10 µm to about 100 µm, and a center to center spacing between adjacent islands being in a range of about 20 µm to about 300 µm, each island comprising one or more layers of an extracellular matrix protein; seeding the pattern of islands with a plurality of mesenchymal progenitor cells and culturing the mesenchymal progenitor cells under conditions that induce adipogenesis of at least one of the mesenchymal progenitor cells, thereby producing adipocyte islands; disposing a fiber layer over the first surface of the support and over the adipocytes on the islands, each fiber layer comprising a plurality of polymer fibers each having a diameter in a range of about 100 nm to about 1 µm; culturing the adipocytes with the fiber layer over the adipocytes under suitable conditions until at least one of the adipocytes grows to a diameter of between about 30 µm and about 300 µm; contacting the adipocyte with a test compound; and determining the effect of the test compound on adipocyte viability, adipocyte hypertrophy, and/or adipocyte function in the presence and absence of the test compound, wherein a modulation of adipocyte viability, adipocyte hypertrophy, and/or adipocyte function in the presence of said test compound as compared to adipocyte viability, adipocyte hypertrophy, and/or adipocyte function in the absence of said test compound indicates that said test compound modulates adipocyte viability, adipocyte hypertrophy, and/or adipocyte function, thereby identifying a compound that modulates adipocyte viability, adipocyte hypertrophy, and/or adipocyte function.

In one aspect, the present invention provides a method for treating a subject needing reconstructive or cosmetic surgery. The method includes providing the mature adipocytes produced according to the methods of the invention, and implanting the cells in the subject, thereby treating the subject requiring reconstructive or cosmetic surgery.

In one aspect, the present invention provides a kit for producing mature adipocytes in vitro. The kit includes a support having a first surface including a pattern of islands, each island having a length, width or diameter in a range of about 10 µm to about 100 µm, and a center to center spacing between adjacent islands being in a range of about 20 µm to about 300 µm, each island comprising one or more layers of a matrix protein, and each island configured to support culture of mesenchymal progenitor cells through adipogenesis of at least one of the mesenchymal stem cells to produce adipocytes on the islands; and a fiber layer configured to be disposed over the first surface of the support and over the cells after adipogenesis of at least one of the cells, the fiber layer comprising a plurality of polymer fibers each having a diameter in a range of about 100 nm to about 1 µm; wherein the support and the fiber layer are configured to support maturation and/or hypertrophy of the adipocytes in culture up to a diameter of between about 30 µm and about 300 µm.

Each island may independently have a length, width, or diameter in a range of about 10 µm to about 60 µm; about 20 µm to about 50 µm; or about 20 µm to about 40 µm.

Each of the polymer fibers may independently comprise greater than about 50 wt % polycaprolactone (PCL). Each of the polymer fibers may independently further comprise about 5 to about 49 wt % gelatin.

Each of the polymer fibers may independently have a diameter in a range of about 400 nm to about 800 nm; or about 420 nm to about 620 nm.

In one embodiment, the fiber layer is attached to a frame having an outer diameter similar to that of a well of a culture plate; and wherein the support is disposed in a well of a culture plate or the support is at least a portion of a bottom surface of the well of the culture plate.

In one embodiment, the kit further comprises one or more additional supports, each having a first surface with a pattern of islands; and one or more additional fiber layers, each fiber layer attached to a corresponding frame, wherein the one or more additional supports are each disposed in a corresponding well of the culture plate or each of the one or more additional supports is at least a portion of a bottom surface of the corresponding well of the culture plate.

In one embodiment, the kit is specifically for culturing adipocytes to a selected final diameter, and wherein a center to center spacing of the islands corresponds to the selected desired final diameter of the adipocytes.

In one aspect, the present invention provides a method of making a support system for producing mature adipocytes in vitro. The method includes providing a support; forming or depositing a pattern of islands on a first surface of the support, each island having a length, width, or diameter in a range of about 10 µm to about 100 µm, and a center to center spacing between adjacent islands being in a range of about 20 µm to about 300 µm, each island comprising one or more layers of a matrix protein; and providing a fiber layer dimensioned to cover the pattern of islands on the first surface of the support after the islands are seeded with mesenchymal progenitor cells, the fiber layer comprising a plurality of polymer fibers each having a diameter in a range of about 100 nm to about 1 µm.

In one embodiment, the islands are patterned by microcontact printing.

Each island may independently have a length, width, or diameter in a range of about 10 µm to about 60 µm; about 20 µm to about 50 µm; or about 20 µm to about 40 µm.

In one embodiment, providing the fiber layer dimensioned to cover the pattern of islands on the first surface of the support after the islands are seeded with preadipocyte cells comprises forming the polymeric fibers by rotary jet spinning a polymer or pull-spinning; and collecting the polymeric fibers on a surface forming a fiber layer.

In one embodiment, the polymeric fibers are collected on a surface of a frame.

In one embodiment, the polymeric fibers are collected on a surface of multiple frames connected to or attached to each other to and the collection of the fibers forms a large fiber layer; and wherein the method further comprises cutting out a layer of fibers corresponding to each frame from the large fiber layer.

In one embodiment, cutting out a layer of fibers corresponding to each frame from the large fiber layer also separates the multiple frames from each other.

Each of the polymer fibers may independently comprise greater than about 50 wt % polycaprolactone (PCL). Each of the polymer fibers may independently further comprise about 5 to about 49 wt % gelatin.

Each of the polymer fibers may independently have a diameter in a range of about 400 nm to about 800 nm; or about 420 nm to about 620 nm.

BRIEF DESCRIPTION OF THE DRAWINGS

FIGS. 1A-1B are micrographs of adipocytes in conventional adherent 2-dimensional culture that were differentiated in vitro from mesenchymal progenitor cells that were, in turn, differentiated in vitro from HUES 9 human embryonic stem cells (RRID:CVCL_0057). Briefly, embryonic stem cells were treated with dispase to form clumps of 10 cells and placed in low-adhesion plastic 6-well dishes (Costar Ultra Low Attachment; Corning Life Sciences) in growth medium containing DMEM, 15% FBS and 1% GlutaMAX for seven days. Resulting embryoid bodies were re-plated on gelatin-coated 6-well dishes in culture medium containing DMEM, 10% FBS and 1% GlutaMAX for five days. Cells were trypsinized (0.25% trypsin) and re-plated on cell culture dishes in medium containing DMEM, 15% FBS, 1% GlutaMAX and 2.5 ng ml$^{-1}$ bFGF (Aldevron) to expand mesenchymal progenitor cells. Mesenchymal progenitor cells were seeded at 200,000 cells per well in 12-well dishes coated for 30 minutes with 0.1% gelatin (Millipore Cat # ES-006-B) in adipogenic differentiation medium containing DMEM, 7.5% knockout serum replacement (KOSR; Invitrogen), 0.5% non-essential amino acids, 1% penicillin and streptomycin, 0.1 µM dexamethasone, 10 µg ml$^{-1}$ insulin (Sigma) and 0.5 µM rosiglitazone for 33 days. The images demonstrate the detachment and folding up of the adipocyte cultures before the cells have reached mature sizes.

FIG. 1C is a graph quantifying the longevity of adipocyte cultures differentiated as described in FIGS. 1A-1B in conventional adherent 2-dimensional culture over time.

FIG. 2A shows the creation of an array of 0.3 mm thick acrylic frames by laser cutting using an Epilog CO2 laser at 6% power, 6% speed, and 2200 frequency. FIG. 2B is a zoom-in of one frame and shows the tabs that allow that press fit locking mechanism into well plates. FIG. 2C shows how fiber layers are spun onto the frame arrays by pull spinning a 6% wt/vol solution of 80% PCL and 20% gelatin dissolved in hexafluoroisopropanol with a rotating bristle at 25,000 rpm. FIG. 2D shows individual fiber layer coated frames after excision from the array by laser cutting using the same conditions as described in FIG. 2A. FIG. 2E shows the fibers inserted into a 12-well plate.

FIGS. 8A-8B are micrographs showing breakdown by adipocytes differentiated from primary human mesenchymal stem cells from adipose tissue (Promocell C-12977) of pull spun fiber layers as described in FIG. 2 with 80% gelatin and 20% polycaprolactone content. White arrows point to gaps in the network with cleaved fibers after 12 days of differentiation, demonstrating fiber layers having too much gelatin do not support adipocyte differentiation and hypertrophy.

DETAILED DESCRIPTION OF THE INVENTION

Figure 1E:
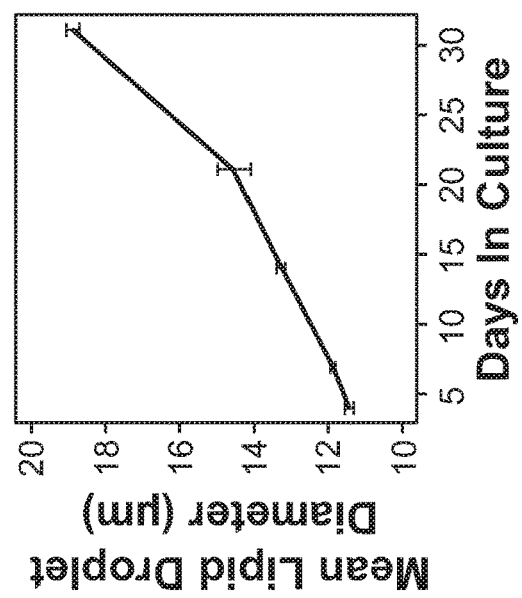
FIG. 1E is a graph quantifying the mean lipid droplet size in human pluripotent stem cell derived adipocytes differentiated as described in FIGS. 1A-1B.
Figure 1D:
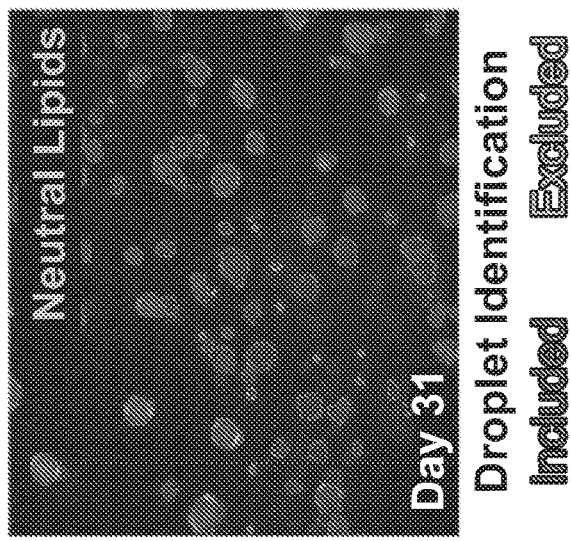
FIG. 1D shows an exemplary fluorescence micrograph of adipocytes stained with the neutral lipid dye to quantify lipid droplet sizes in human pluripotent stem cell derived adipocytes differentiated as described in FIGS. 1A-1B. Lipid droplets were identified automatically by image analysis software on the ThermoFisher ArrayScan XTI, which was also used to estimate cell size. A minimum size threshold was used to exclude identified objects that were too small to reliably report on cell size. Identified droplets that were included in size calculations are outlined in gray, while those that were excluded are outlined in light gray.
Figure 1F:
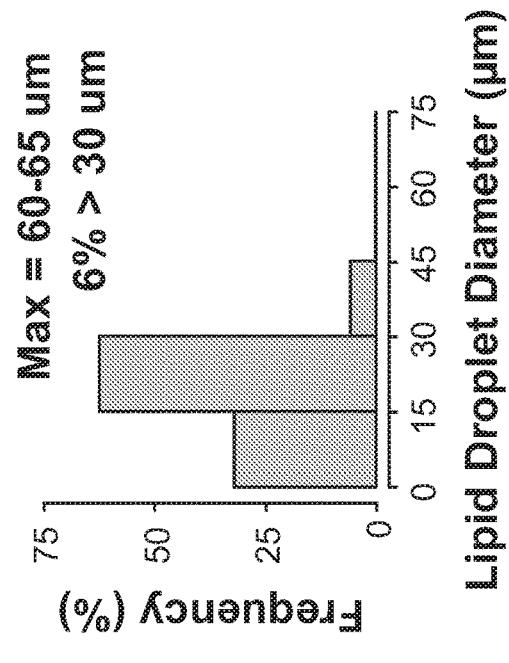
FIG. 1F is a histogram showing the size distribution of human pluripotent stem cell derived adipocytes differentiated as described in FIGS. 1A-1B. Only 6% of the cells are larger than 30 microns in diameter at Day 31 of differentiation.
Figure 3:
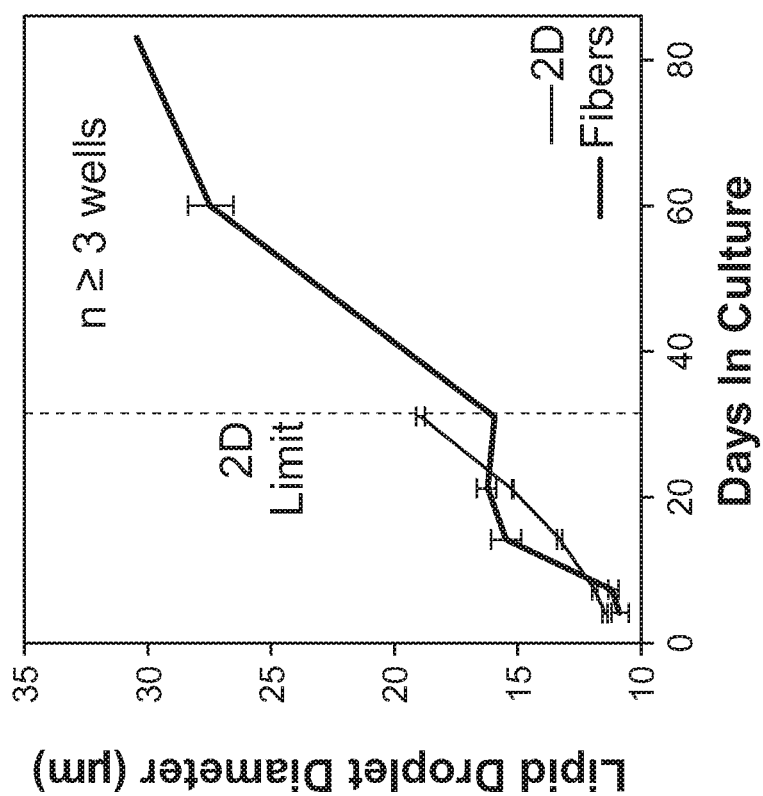
FIG. 3 is a graph comparing the mean lipid droplet size in HUES 9 human embryonic stem cell-derived adipocytes differentiated using the same induction media as in FIGS. 1A-1B but also having a fiber layer disposed over the adipocytes, each fiber layer comprising a plurality of polymer fibers each having a diameter in a range of about 100 nm to about 1 µm (prepared as described in FIG. 2) to those cultured by conventional methods (vertical line; and as described in FIGS. 1A-1B). The figure demonstrates that the fiber layer extends the lifespan of adipocyte cultures and supports average adipocyte sizes beyond the limits of conventional culture (gray line).
Figure 4B:
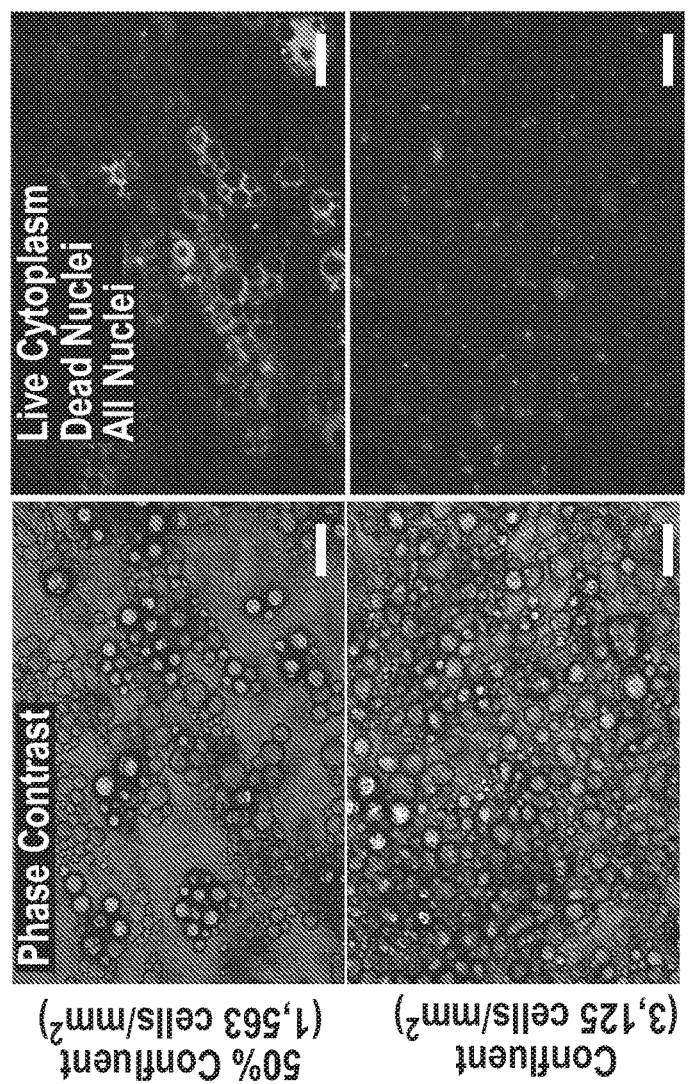
FIG. 4B shows example phase contrast and fluorescent micrographs of 2 ug/mL Calcein (white and light gray; live cell marker), 1 ug/mL Hoechst (medium gray; nuclear marker), and 1 ug/mL propidium iodide (dark gray, dead cell marker) stained live adipocytes following 83 days of differentiation having a fiber layer disposed over the adipocytes as described in FIG. 4A. Cultures seeded at confluence and 50% confluence are shown.
Figure 4A:
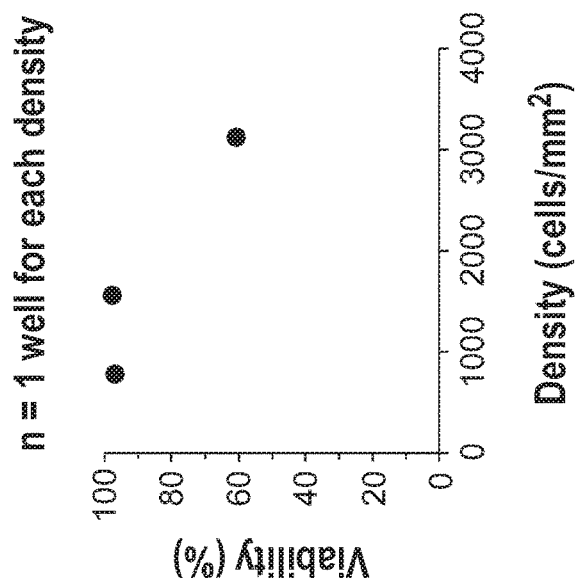
FIG. 4A is a graph quantifying survival of adipocytes derived from HUES 9 embryonic stem cells differentiated and had a fiber layer disposed over the adipocytes as described in FIG. 3 as a function of seeding density following 83 days of differentiation.
Figure 5:
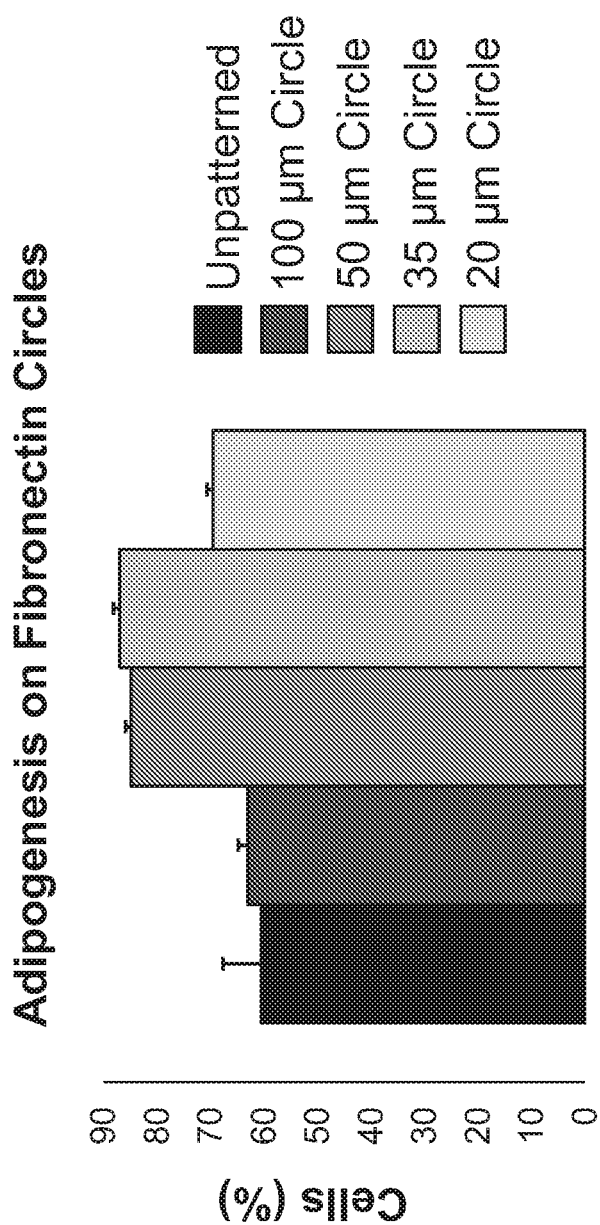
FIG. 5 is a graph quantifying differentiation efficiency of HUES 9 adipocytes differentiated using the same media as described in FIGS. 1A-1B as a function of cell seeding density in either conventional unpatterned cell culture or culture with cells on patterned fibronectin islands with diameters between 20 and 50 um. The fibronectin islands were produced by stamping onto the bottom of a 12-well plate a Dow Sylgard 184 polydimethylsiloxane stamp that was mixed and cured per manufacturer's specifications on an SU-8 inverse island pattern on a silicon wafer. The SU-8 pattern was created on the silicon wafer by soft lithography using the manufacturer's protocol for 3005 series SU-8 on a three-inch silicon wafer and a custom photomask with circular islands that blocked UV exposure to the areas in the shown pattern. The adipocyte transcription factor C/EBP-α was immunostained and used as a differentiation marker and at least 100 cells from 2 to 8 wells were counted per condition.
Figure 6:
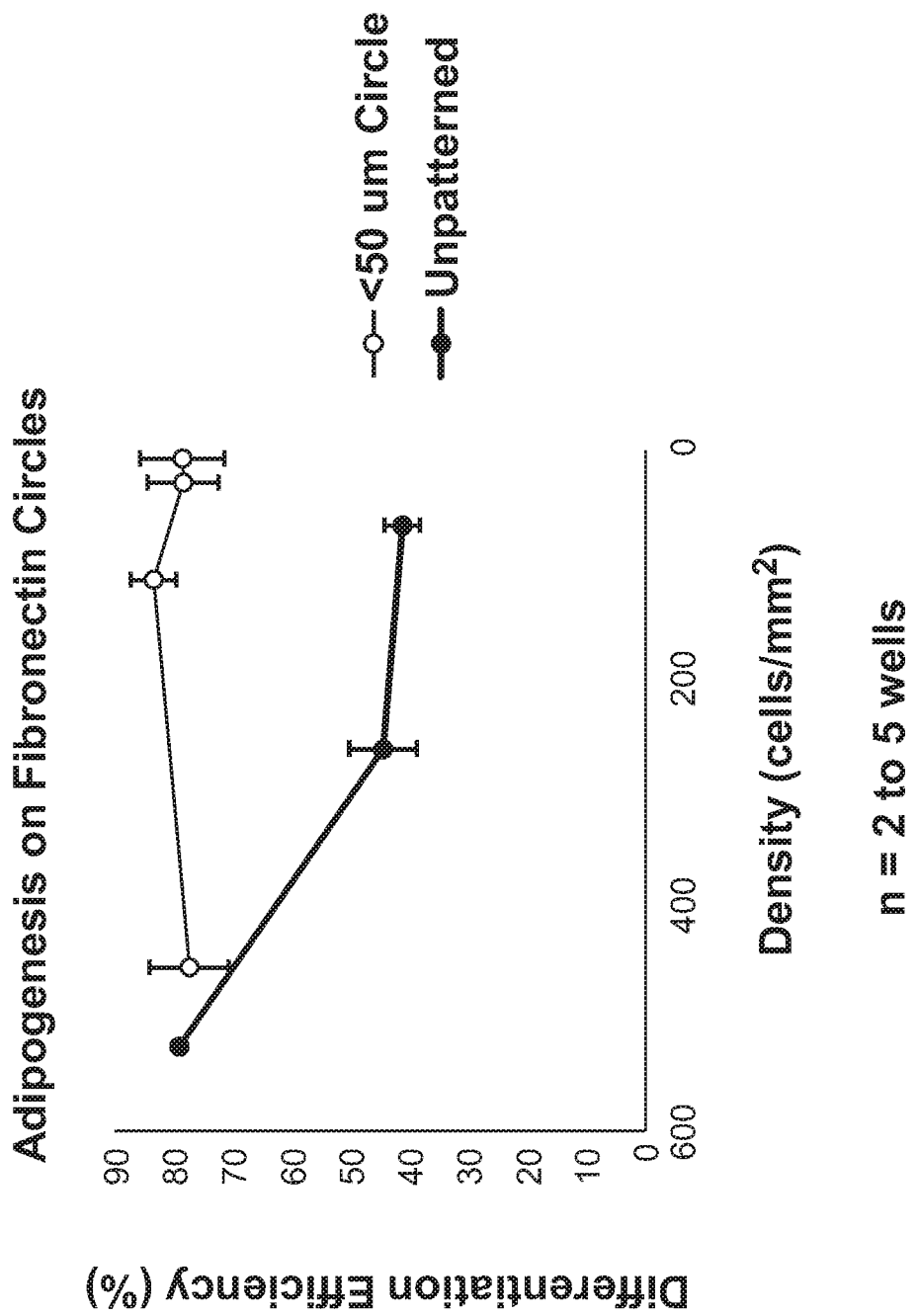
FIG. 6 is a graph quantifying differentiation efficiency of HUES 9 adipocytes differentiated using the same media as described in FIGS. 1A-1B as a function of cell seeding density in either conventional unpatterned cell culture or cells patterned on fibronectin islands with diameters between 20 and 50 um. The fibronectin islands were produced by stamping onto the bottom of a 12-well plate a Dow Sylgard 184 polydimethylsiloxane stamp that was mixed and cured per manufacturer's specifications on an SU-8 inverted island pattern on a silicon wafer. The SU-8 pattern was created on the silicon wafer by soft lithography using the manufacturer's protocol for 3005 series SU-8 on a three inch silicon wafer and a custom photomask with circular islands that blocked UV exposure to the areas in the shown pattern. The adipocyte transcription factor C/EBP-α was immunostained and used as a differentiation marker and at least 100 cells from 2 to 5 wells were counted per condition.
Figure 7:
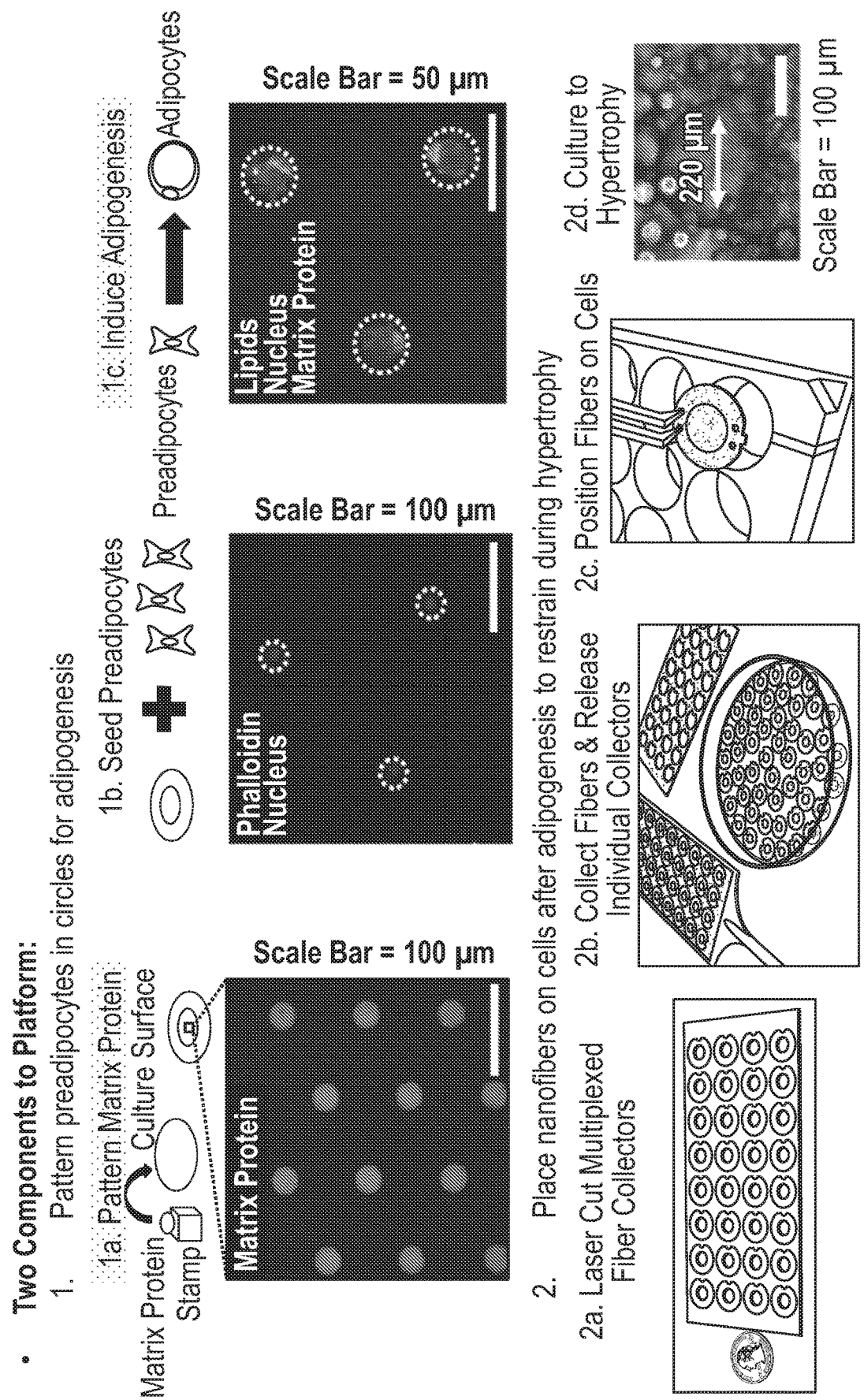
FIG. 7 depicts the steps in an exemplary embodiment of the methods of the invention. In Step 1, preadipocytes are patterned into circles to promote adipogenesis. Step 1a shows the patterning of extracellular matrix proteins (dark gray circles) onto a culture surface (black) by microcontact printing using a Dow Sylgard 184 polydimethylsiloxane stamp (light gray) prepared per manufacturers' protocols. Below the illustration, an actual pattern of 35 um diameter circular islands with 100 um center-to-center spacing was used to print 50 ug/mL laminin on a glass coverslip and visualized by immunostaining. Step 1b shows the seeding of Hues 9 mesenchymal progenitor cells onto a micropatterned substrate. Below the illustration, a Hoechst and Phalloidin stained image shows the nuclei (light gray) and filamentous actin (medium gray) of cells attached to 35 um diameter islands with 200 um center-to-center spacing (outlined by white dotted circles). Step 1c shows patterned cells following 11 days of adipocyte differentiation using the media described in FIGS. 1A-1B. Nuclei of cells patterned as in Step 1a were immunostained with the adipocyte transcription factor PPARG and lipid droplets were stained with a neutral lipid dye (medium and dark gray). In Step 2, a fiber network is disposed on top of patterned adipocytes after two days of differentiation. Step 2a is the creation of an array of 0.5 mm thick plastic frames by laser cutting using an Epilog $CO_2$ laser at 6% power, 6% speed, and 2200 hertz. Nanofibers are spun onto the array of frames and individually excised from the array by a laser cutting as described in FIG. 2b. In Step 2c, an individual fiber layer coated frame is inserted and locked into a well plate by a press fit. In Step 2d, adipocytes are cultured for 1-6 months to allow hypertrophic growth.
Figures 9A, 9B:
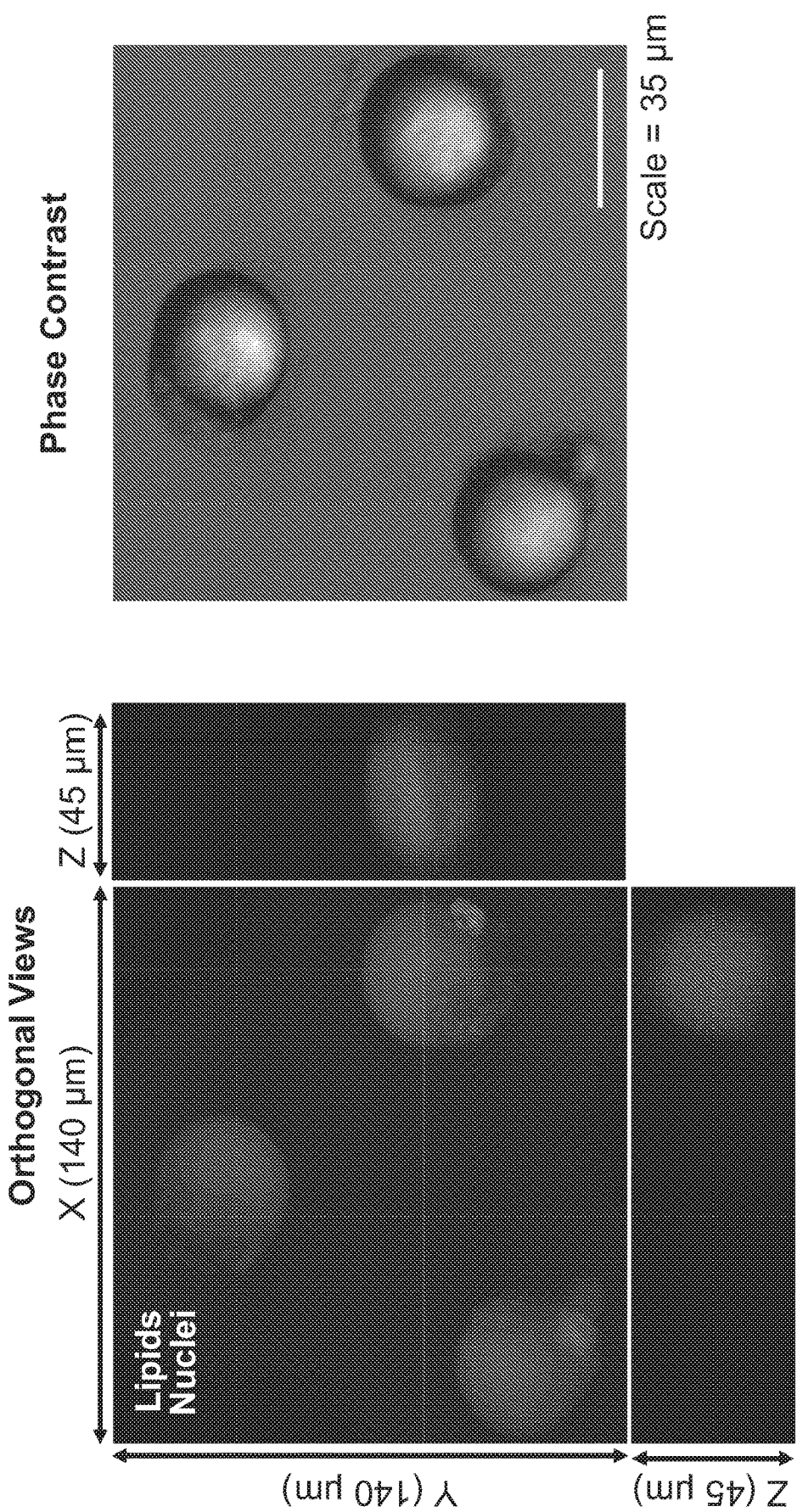
FIG. 9A shows a max projection z-stack of confocal micrographs and orthogonal views of adipocytes differentiated from primary human mesenchymal stem cells from adipose tissue (Promocell C-12977) for 30 days on 35 um diameter fibronectin islands and under 80% polycaprolactone/20% gelatin fiber networks using the adipogenic media described in FIG. 1. Adipocytes were stained for the adipocyte transcription factor C/EBP-α (green nuclei) and neutral lipids (red lipid droplets).
FIG. 9B is a phase contrast image of the same cells shown in FIG. 9A.
Figure 10:
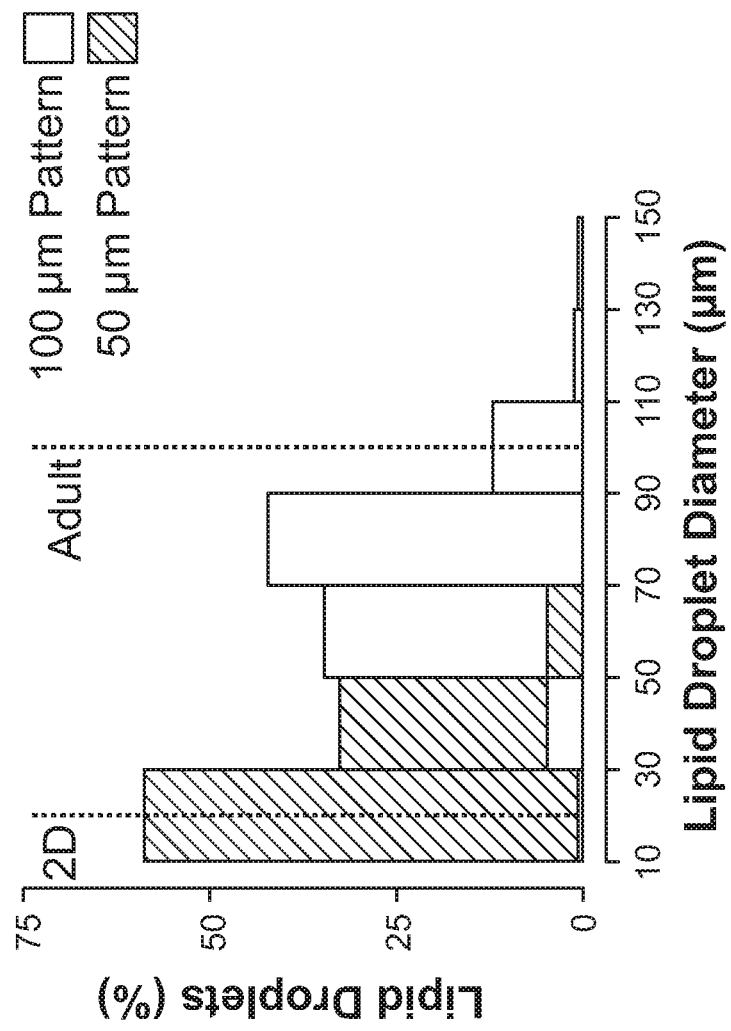
FIG. 10 is a histogram showing the distribution of adipocyte sizes differentiated in vitro from primary human mesenchymal stem cells from adipose tissue (Promocell C-12977) for 92 days in the same adipogenic medium described in FIGS. 1A-1B on 35 um diameter fibronectin islands and under 80% polycaprolactone/20% gelatin fiber layers. The solid bars represent cells cultured on 100 um center-to-center spaced islands, and the bars with the hatches represent cells cultured on 50 um center-to-center spaced islands. Vertical lines indicate the average adipocyte sizes for adipocytes differentiated by conventional methods and for adipocytes observed in adult humans.

The present invention is based, at least in part, on the discovery of methods and systems that support adipocyte differentiation and growth of mesenchymal progenitor cells and enable adipocyte hypertrophy (or an increase in the size of the cells) so that mature human adipocytes are produced in vitro.

In particular, methods and systems which accommodate 3-dimensional adipocyte expansion and which include protein micropatterning to position and coax differentiation of pre-adipocytes with a polymer fiber layer that covers and restrains the micropatterned adipocytes during maturation and hypertrophic growth have been discovered. The fiber layer extends the lifespan of adipocyte cultures from one to over six months and increased average cell size over 50-fold relative to conventional culture. In addition, it has been discovered that the spacing between adipocytes in the micropattern controls the rate of hypertrophy independent of time in culture and this parameter can be used to tune adipocyte size in the synthetic tissue.

I. Definitions

In order that the present invention may be more readily understood, certain terms are first defined. In addition, it should be noted that whenever a value or range of values of a parameter are recited, it is intended that values and ranges intermediate to the recited values are also part of this invention.

In the following description, for purposes of explanation, specific numbers, materials and configurations are set forth in order to provide a thorough understanding of the invention. It will be apparent, however, to one having ordinary skill in the art that the invention may be practiced without these specific details. In some instances, well-known features may be omitted or simplified so as not to obscure the present invention. Furthermore, reference in the specification to phrases such as "one embodiment" or "an embodiment" means that a particular feature, structure or characteristic described in connection with the embodiment is included in at least one embodiment of the invention. The appearances of phrases such as "in one embodiment" in various places in the specification are not necessarily all referring to the same embodiment.

The articles "a" and "an" are used herein to refer to one or to more than one (i.e., to at least one) of the grammatical object of the article. By way of example, "an element" means one element or more than one element.

The term "comprising" or "comprises" is used herein in reference to compositions, methods, and respective component(s) thereof, that are essential to the disclosure, yet open to the inclusion of unspecified elements, whether essential or not.

The term "consisting of" refers to compositions, methods, and respective components thereof as described herein, which are exclusive of any element not recited in that description of the embodiment.

The term "adipocytes," also known as lipocytes or fat cells, are the cells that primarily compose adipose tissue and are specialized in storing energy as fat.

"Mature adipocytes" can be distinguished from adipocytes that are not mature based on cell diameter, cell volume, and/or lipid droplet diameter within the cell. Accordingly, "mature adipocytes" include adipocytes that have a diameter of about 50 μm to about 130 μm in an adult human subject and those that have a diameter of about 90 μm to about 280 μm in an obese human subject (see, e.g., Table 1), e.g., a human subject having a body mass index (BMI) greater than about 30, while those adipocytes which are not mature adipocytes have a diameter of about 40 μm to about 130 μm (see, e.g., Table 1). In some embodiments of the invention, the methods include producing mature adipocytes having a diameter of about 90 μm to about 280 μm, 90 μm to about 270 μm, 90 μm to about 260 μm, 90 μm to about 250 μm, 90 μm to about 240 μm, 90 μm to about 230 μm, 90 μm to about 220 μm, 90 μm to about 210 μm, 90 μm to about 200 μm, 90 μm to about 190 μm, a diameter of about 90 μm to about 180 μm, 90 μm to about 170 μm, 90 μm to about 160 μm, 90 μm to about 150 μm, 90 μm to about 140 μm, 90 μm to about 130 μm, 90 μm to about 120 μm, 90 μm to about 110 μm, about 100 μm to about 280 μm, 100 μm to about 270 μm, 100 μm to about 260 μm, 100 μm to about 250 μm, 100 μm to about 240 μm, 91000 μm to about 230 μm, 100 μm to about 220 μm, 100 μm to about 210 μm, 100 μm to about 200 μm, 100 μm to about 190 μm, a diameter of about 100 μm to about 180 μm, 100 mm to about 170 μm, 100 μm to about 160 μm, 100 μm to about 150 μm, 100 μm to about 140 μm, 100 μm to about 130 μm, 100 μm to about 120 μm, 100 μm to about 110 μm. Ranges and values intermediate to the above recited ranges and values are also contemplated to be part of the invention.

"Mature adipocytes" also include adipocytes having a mean cell volume of about 382,000 μm$^3$ to about 3,054,000 μm$^3$ (see, e.g., Table 1), while those adipocytes which are not mature adipocytes have a mean cell volume of about 48,000 μm$^3$ to about 697,000 μm$^3$ (see, e.g., Table 1)

The term "body mass index" refers to a weight-to-height ratio, calculated by dividing the weight in kilograms or pounds of a subject by the square of the subject's height in meters or inches, respectively, which is used as an indicator of obesity and underweight. For example, a subject have a BMI below about 18.5 is considered to be underweight; a subject having a BMI of about 18.5 to about 24.9 is considered to be normal; and a subject having a BMI of about 30 or higher is considered to be obese.

The term "hypertrophy" refers to an increase in the size of adipocytes.

II. Methods of the Invention

The present invention provides methods for the differentiation and growth of preadipocytes or mesenchymal progenitor cells that enable the production of mature human adipocytes in vitro that overcome the limitation of art known culturing methods.

Accordingly, in one aspect, the present invention provides methods for producing mature adipocytes in vitro. The methods include providing a support having a first surface including a pattern of islands, each island having a length, width, or diameter in a range of about 10 μm to about 100 μm, and a center to center spacing between adjacent islands being in a range of about 20 μm to about 300 μm, each island comprising one or more layers of an extracellular matrix protein; seeding the pattern of islands with a plurality of mesenchymal progenitor cells and culturing the mesenchymal progenitor cells under conditions that induce adipogenesis of at least one of the mesenchymal progenitor cells, thereby producing adipocyte islands; disposing a fiber layer over the first surface of the support and over the adipocytes on the islands, each fiber layer comprising a plurality of polymer fibers each having a diameter in a range of about 100 nm to about 1 μm; and culturing the adipocytes with the fiber layer over the adipocytes under suitable conditions until at least one of the adipocytes grows to a diameter of between about 30 μm and about 300 μm, thereby generating mature adipocytes in vitro.

Suitable supports for use in the methods and compositions of the invention include a silicon wafer, a glass cover slip, a multi-well plate or multi-well tissue culture plate. A support may be formed of a rigid or semi-rigid material, such as a metal, ceramic, or a combination thereof. In particular embodiments, the Young's modulus of the support material used to form the base layer is about 0.1 to about 10 kiloPascal (kPa), e.g., any material that is tuned to mimic the native (in vivo) stiffness of adipocytes. The native stiffness of adipocytes may be considered to be between about 0.1 kiloPascal (kPa) and about 10.0 kPa; between about 0.1 kPa and about 7.5 kPa; between about 0.1 kPa and about 5 kPa; between about 0.1 kPa and about 2.5 kPa; between about 0.1 kPa and about 1 kPa; e.g., about 0.1, 0.5, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10.0 kPa. Ranges and values intermediate to the above recited ranges and values are also contemplated to be part of the invention.

The support material may also be transparent, so as to facilitate observation. Examples of suitable support materials include polymethylmethacrylate, polystyrene, polycarbonate, polyethylene terephthalate film, silicon wafer, or gold. In one embodiment, the base layer is a silicon wafer, a glass cover slip, a multi-well plate, a multi-well tissue culture plate, silicone, a polydimethylsiloxane layer, a device, a microfluidic chip, hydroxyapatite, or any material mimicking soft tissue or used for medical implants or food.

In one embodiment, the support comprises the well of a tissue culture plate. A schematic representation of such device is shown in FIG. 2E.

The islands may have a length, width, or diameter in a range of about 10 μm to about 100 μm; about 10 μm to about 60μ; about 20 μm to about 50 μm; or about 20 μm to about 40 μM.

The islands may have a center to center spacing between adjacent islands being in a range of about 20 μm to about 250 μm; about 20 μm to about 200 μm; or about 20 μm to about 150 μm. The islands may be any suitable shape and are preferably substantially circular in shape.

The islands include one or more layers of an extracellular matrix protein or a plurality of extracellular matrix (ECM) proteins, e.g., two or more, three or more, four or more, five or more, or six or more ECM proteins.

Suitable ECM proteins include a collagen, a laminin, and a fibronectin, or a fragment thereof, and a combination thereof. In one embodiment, the ECM protein is encoded by a gene selected from the group consisting of genes COL6A3, COL6A1, SPP1, COL6A2, LAMC2, COL1A2, FNDC3A, BGN, COL1A1, LAMB1, LAMC1, COL18A1, SPARC, LAMB3, FN1, TNC, FNDC3B, COL3A1, EMILIN1, COL6A6, AGRN, LAMA4, COL28A1, LAMA3, LAMA5, LAMC3, FBN1, LAMB2, COL5A1, or a fragment thereof, and a combination thereof. In another embodiment, the ECM protein is encoded by a gene selected from the group consisting of genes COL6A3 and COL6A1.

The pattern of islands on the support may be prepared by methods known to one of ordinary skill in the art and include, for example, mircopatterning of the support using microcontact printing of the ECM protein, e.g., using a stamp, or a photomask having the pattern of islands and placed on the support to cover portions of the support that are outside the pattern. A mask blocking areas of the support prior to applying a uniform coat may be used and subsequently removed to reveal the pattern. Laser or other types of ablation may also be used to etch a pattern in the support to from a uniform layer. Three-dimensional grooves, e.g., micromolded three-dimensional grooves, may also be used.

To attach cells, a support comprising the pattern of islands is placed in culture with a cell suspension allowing the cells to settle and adhere and bind to the ECM proteins. Examples of cell types that may be used include cells that will differentiate into adipocytes, e.g., stem cells, e.g., embryonic stem cells or adult stem cells, or progenitor cells.

Seeding of cells may be performed according to standard methods.

Suitable cells for use in the invention may be normal cells, abnormal cells (e.g., those derived from a diseased tissue, or those that are physically or genetically altered to achieve an abnormal or pathological phenotype or function), normal or diseased adipocytes, stem cells (e.g., embryonic stem cells), or induced pluripotent stem cells.

Cells for seeding can be cultured in vitro, derived from a natural source, genetically engineered, or produced by any other means. Any natural source of eukaryotic cells may be used. Embodiments in which a scaffold is implanted in an organism can use cells from the recipient, cells from a conspecific donor or a donor from a different species.

The term "progenitor cell" is used herein to refer to cells that have a cellular phenotype that is more primitive (e.g., is at an earlier step along a developmental pathway or progression than is a fully differentiated cell) relative to a cell which it can give rise to by differentiation. Often, progenitor cells also have significant or very high proliferative potential. Progenitor cells can give rise to multiple distinct differentiated cell types or to a single differentiated cell type, depending on the developmental pathway and on the environment in which the cells develop and differentiate.

The term "progenitor cell" is used herein to refer to cells that have a cellular phenotype that is more primitive (e.g., is at an earlier step along a developmental pathway or progression than is a fully differentiated cell) relative to a cell to which it can give rise by differentiation. Often, progenitor cells also have significant or very high proliferative potential. Progenitor cells can give rise to multiple distinct differentiated cell types or to a single differentiated cell type, depending on the developmental pathway and on the environment in which the cells develop and differentiate.

The term "progenitor cell" is used herein synonymously with "stem cell."

The term "stem cell" as used herein, refers to an undifferentiated cell that is capable of proliferation and giving rise to more progenitor cells having the ability to generate a large number of mother cells that can in turn give rise to differentiated, or differentiable daughter cells. The daughter cells themselves can be induced to proliferate and produce progeny that subsequently differentiate into one or more mature cell types, while also retaining one or more cells with parental developmental potential. The term "stem cell" refers to a subset of progenitors that have the capacity or potential, under particular circumstances, to differentiate to a more specialized or differentiated phenotype, and which retains the capacity, under certain circumstances, to proliferate without substantially differentiating. In one embodiment, the term stem cell refers generally to a naturally occurring mother cell whose descendants (progeny) specialize, often in different directions, by differentiation, e.g., by acquiring completely individual characters, as occurs in progressive diversification of embryonic cells and tissues. Cellular differentiation is a complex process typically occurring through many cell divisions. A differentiated cell may derive from a multipotent cell which itself is derived from a multipotent cell, and so on. While each of these multipotent cells may be considered stem cells, the range of cell types each can give rise to may vary considerably. Some differentiated cells also have the capacity to give rise to cells of greater developmental potential. Such capacity may be natural or may be induced artificially upon treatment with various factors. In many biological instances, stem cells are also "multipotent" because they can produce progeny of more than one distinct cell type, but this is not required for "stem-ness." Self-renewal is the other classical part of the stem cell definition. In theory, self-renewal can occur by either of two major mechanisms. Stem cells may divide asymmetrically, with one daughter retaining the stem state and the other daughter expressing some distinct other specific function and phenotype. Alternatively, some of the stem cells in a population can divide symmetrically into two stems, thus maintaining some stem cells in the population as a whole, while other cells in the population give rise to differentiated progeny only. Formally, it is possible that cells that begin as stem cells might proceed toward a differentiated phenotype, but then "reverse" and re-express the stem cell phenotype, a term often referred to as "dedifferentiation" or "reprogramming" or "retrodifferentiation".

The term "embryonic stem cell" is used to refer to the pluripotent stem cells of the inner cell mass of the embryonic blastocyst (see U.S. Pat. Nos. 5,843,780, 6,200,806, the contents of which are incorporated herein by reference). Such cells can similarly be obtained from the inner cell mass of blastocysts derived from somatic cell nuclear transfer (see, for example, U.S. Pat. Nos. 5,945,577, 5,994,619, 6,235,970, which are incorporated herein by reference). The distinguishing characteristics of an embryonic stem cell define an embryonic stem cell phenotype. Accordingly, a cell has the phenotype of an embryonic stem cell if it possesses one or more of the unique characteristics of an embryonic stem cell such that that cell can be distinguished from other cells. Exemplary distinguishing embryonic stem cell characteristics include, without limitation, gene expression profile, proliferative capacity, differentiation capacity, karyotype, responsiveness to particular culture conditions, and the like.

The term "adult stem cell" or "ASC" is used to refer to any multipotent stem cell derived from non-embryonic tissue, including fetal, juvenile, and adult tissue. Stem cells have been isolated from a wide variety of adult tissues including blood, bone marrow, brain, olfactory epithelium, skin, pancreas, skeletal muscle, and cardiac muscle. Each of these stem cells can be characterized based on gene expression, factor responsiveness, and morphology in culture. Exemplary adult stem cells include neural stem cells, neural crest stem cells, mesenchymal stem cells, hematopoietic stem cells, and pancreatic stem cells.

In one embodiment, suitable progenitor cells for use in the methods and compositions of the invention are mesenchymal progenitor cells. Mesenchymal progenitor cells are multipotent stromal cells that can differentiate into a variety of cell types, including osteoblasts (bone cells), chondrocytes (cartilage cells), myocytes (muscle cells) and adipocytes. Mesenchymal progenitor cells can be obtained from bone marrow, umbilical cord tissue, in particular, Wharton's jelly and umbilical cord blood, adipose tissue, the developing tooth bud of the mandibular third molar, and amniotic fluid.

Isolated adipose tissue (such as white adipose tissue), isolated cells (such as primary adipocytes or adipocyte cell lines), or a combination thereof may be employed. In some methods, an adipose cell-line may be employed. Exemplary cells include, but are not limited to, 3T3-L1 cells, SGBS, T37i cells, 3T3-F442A cells, and/or HIB-1B cells. Any of a variety of isolated cells (such as cell lines) from any organism can be used. In addition, synthetic lipid droplets or other lipid bearing organelles or emulsified lipids without an organismal membrane that can be grown by lipid accumulation or otherwise positioned into patterns are also contemplated to be part of the invention.

The aforementioned cells/cell-lines may be optionally transformed to express a variety of growth factors and/or agents. The reagents and markers useful for such purposes are known in the art. See, U.S. Pat. Nos. 5,598,501 and 6,501,598, which are incorporated by reference herein.

In one embodiment, in the methods and compositions of the invention adipocytes maintain their viability and functionality for greater than 40 days, greater than 50 days, greater than 60 days, greater than 70 days, greater than 80 days, greater than 90 days, greater than 100 days, greater than 110 days, greater than 120 days, greater than 130 days, greater than 140 days, greater than 150 days, greater than 160 days, greater than 170 days, or greater than 180 days, or more, e.g., about 40, 50, 60, 70, 80, 90, 100, 110, 120, 130, 140, 150, 160, 170, 180, 190, 200 days, or more.

In some embodiments, the cells are cultured as described herein for about 3 months and to a mature size, e.g., about 90 to about 100 um in diameter.

In one embodiment, mesenchymal progenitor cells are seeded at a density of between about 1,000 cells/cm2 and 60,000 cells/cm2 (×2 of conventional confluent culture). In preferred embodiments, the cells are seeded at a density of about is 2,500 to about 11,500 cells/cm2. Values and ranges intermediate to the above-recited values and ranges are also contemplated by the present invention.

Any suitable method may be used to prepare the fiber layer. Exemplary methods are described herein and also include, for example, electrospinning, wet spinning, air spinning, etc. For example, a method for generating the fiber layer may include configuring micron, submicron or nanometer dimension polymeric fibers in a desired shape using a collection device, such as depicted in FIG. 2.

Any suitable method may be used to prepare the non-woven polymeric fiber sheets. For example, a method for generating the non-woven polymeric fiber sheet may include configuring micron, submicron or nanometer dimension polymeric fibers in a desired shape using a collection device, such as a glass coverslip, a multi-well plate, a mandrel or a mandrel assembly.

In one embodiment, non-woven polymeric fiber sheets are formed by ejecting a polymer solution from a reservoir onto a multi-well plate. In another embodiment, non-woven polymeric fiber sheets are formed by ejecting a polymer solution from a reservoir onto a rotating mandrel or mandrel assembly. In exemplary embodiments, rotary jet spinning (RJS) is used to create the non-woven polymeric fiber sheets. Suitable RJS devices and uses of the devices for fabricating the non-woven polymeric fiber sheets are described in U.S. Patent Publication No. 2012/0135448, U.S. Patent Publication No. 2013/0312638, U.S. Patent Publication No. 2014/0322515, the entire contents of each of which are incorporated in their entirety by reference.

In other exemplary embodiments, the polymeric fibers may be flung using a pull spinning technique onto a collection device, such as a glass coverslip, a multi-well plate, a mandrel or a mandrel assembly. In one embodiment, non-woven polymeric fiber sheets are formed by flinging a polymer solution from a reservoir onto a multi-well plate. In another embodiment, non-woven polymeric fiber sheets are formed by flinging a polymer solution from a reservoir onto a rotating mandrel or mandrel assembly. Suitable pull spinning devices and uses of the devices for fabricating the non-woven polymeric fiber sheets are described in U.S. Patent Publication No. 2014/0322515, the entire contents of which is incorporated in its entirety by reference, and an exemplary device and method of preparing the sheets are depicted in FIG. 2.

Methods and conditions to induce mesenchymal progenitor cells to differentiate into adipocytes are known in the art and include, for example, the culture conditions described herein, and those described in, e.g., Ahfeldt, et al. (2012) *Nat Cell Biol.* 14(2): 209-219).

The cells on the substrates are cultured in an incubator under physiologic conditions (e.g., at 37° C.) until the preadipocytes on the single-cell islands differentiate into adipocytes. For example, once the cells are seeded, the cells will attach to the islands in about one to two hours and within about 2 days (about 48 hours), the cells have differentiated into adipocytes. At about 4 days (or about 96 hours), cells that are about 20 um in diameter will begin to float away and at about 10 days after seeding about 50% of the seeded cells have floated away. Accordingly, the fiber layer may be disposed or placed over the first surface of the support and over the adipocytes on the islands at about 1 to 2 hours after seeding, or at about 5 to 10 hours after seeding, or at about 12 to 24 hours after seeding, or at about 24 to 48 hours after seeding, or at about 24 to 72 hours after seeding, or at about 49 to 96 hours after seeding. The fiber layer may or may not be in contact with all of the cells on adipocyte islands when placed, however, over time, as the cells on the islands increase in size at least a portion of the cells may be in contact with the fiber layer.

The fiber layer includes a plurality of polymer fibers each polymeric fiber independently having a diameter in a range of about 100 nm to about 1 µm; about 400 nm to about 800 nm; or about 420 to about 620 nm.

The fiber layer includes a porous, three dimensional network, or mesh, of a plurality of polymeric fibers of any orientation including random orientation which are capable of supporting cells disposed underneath. The fiber layer of a plurality of randomly orientated polymeric fibers may be in the form of non-woven polymeric fiber sheets which are held together by fiber-to-fiber interactions and have a desired size and shape, e.g., a desired size and shape suitable for the use thereof. The term "sheet" as used herein refers to a structure having a third dimension substantially less than that of the other two dimensions.

Suitable polymers for use in the polymeric fibers and fiber layers in the methods and compositions of the invention include synthetic and biogenic polymers, and combinations thereof.

Suitable synthetic polymers include, for example, poly (urethanes), poly(siloxanes) or silicones, poly(ethylene), poly(vinyl pyrrolidone), poly(2-hydroxy ethyl methacrylate), poly(N-vinyl pyrrolidone), poly(methyl methacrylate), poly(vinyl alcohol), poly(acrylic acid), polyacrylamide, poly(ethylene-co-vinyl acetate), poly(ethylene glycol), poly (methacrylic acid), polylactides (PLA), polyglycolides (PGA), poly(lactide-co-glycolides) (PLGA), polyanhydrides, polyphosphazenes, polygermanes, polyorthoesters, polyesters, polyamides, polyolefins, polycarbonates, polyaramides, polyimides, polycaprolactone (PCL), and copolymers and derivatives thereof, and combinations thereof.

Suitable biogenic polymers (or bio-derived polymers), e.g., proteins, polysaccharides, lipids, nucleic acids or combinations thereof, include, but are not limited to, silk (e.g., fibroin, sericin, etc.), keratins (e.g., alpha-keratin which is the main protein component of hair, horns and nails, beta-keratin which is the main protein component of scales and claws, etc.), elastins (e.g., tropoelastin, etc.), fibrillin (e.g., fibrillin-1 which is the main component of microfibrils, fibrillin-2 which is a component in elastogenesis, fibrillin-3 which is found in the brain, fibrillin-4 which is a component in elastogenesis, etc.), fibrinogen/fibrins/thrombin (e.g., fibrinogen which is converted to fibrin by thrombin during wound healing), fibronectin, laminin, collagens (e.g., collagen I which is found in skin, tendons and bones, collagen II which is found in cartilage, collagen III which is found in connective tissue, collagen IV which is found in vascular basement membrane, collagen V which is found in hair, etc.), collagen VI which is found in pancreatic islets and adipose, vimentin, neurofilaments (e.g., light chain neurofilaments NF-L, medium chain neurofilaments NF-M, heavy chain neurofilaments NF-H, etc.), amyloids (e.g., alpha-amyloid, beta-amyloid, etc.), actin, myosins (e.g., myosin I-XVII, etc.), titin which is the largest known protein (also known as connectin), gelatin, chitin which is a major component of arthropod exoskeletons, hyaluronic acid which is found in extracellular space and cartilage (e.g., D-glucuronic acid which is a component of hyaluronic acid, D-N-acetylglucosamine which is a component of hyaluronic acid, etc.), etc., and combinations thereof. Exemplary biogenic polymers, e.g., glycosaminoglycans (GAGs) (carbohydrate polymers found in the body), for use in the present invention include, but are not limited to, heparan sulfate founding extracellular matrix, chondroitin sulfate which contributes to tendon and ligament strength, keratin sulfate which is found in extracellular matrix, etc.

The polymeric fibers or fiber layer for use in the present invention may further comprise at least one extracellular matrix (ECM) protein. In some embodiment, the polymeric fibers or fiber layer comprise a plurality of extracellular matrix (ECM) proteins, e.g., two or more, three or more, four or more, five or more, or six or more ECM proteins. The ECM protein may be integral to the fibers (e.g., included in a polymer solution used to prepare the fiber layer (described below) or the ECM protein may be coated on the fibers or coated on the fiber layer.

In one embodiment, the polymeric fibers and fiber layer comprise polycaprolactone (PCL). In one embodiment, the polymeric fibers and fiber layer comprise gelatin. In one embodiment, the polymeric fibers and fiber layer comprise PCL and gelatin. In one embodiment, the polymeric fibers and fiber layer comprise greater than about 50 wt % PCL. In one embodiment, the polymeric fibers and fiber layer comprise about 5 to about 49 wt % gelatin. In a preferred embodiment, the polymeric fibers and fiber layer comprise about 70% PCL: and about 30% gelatin.

In one embodiment, the diameter of the polymeric fibers forming the fiber layer is substantially uniform and is between about 100 nm and about 1000 nm. In another embodiment, the diameter of the polymeric fibers forming the fiber layer is substantially uniform and is between about 400 nm and about 800 nm. In yet another embodiment, the diameter of the polymeric fibers forming the fiber layer is substantially uniform and is between about 420 nm and about 620 nm. Sizes and ranges intermediate to the recited diameters are also part of the invention.

The polymeric fibers may be of any length. In one embodiment, the length of the polymeric fibers is dependent on the length of time the device used to generate the fibers is in motion and/or the amount of polymer fed into the system.

The thickness of the fiber layer may be between about 75 nm and about 5 µm; between about 75 nm and about 1 µm; between about 70 nm and about 5 µm; between about 70 nm and about 1 µm; between about 65 nm and about 5 µm; between about 65 nm and about 1 µm; between about 60 nm and about 5 µm; between about 60 nm and about 1 µm; between about 55 nm and about 5 µm; between about 55 nm and about 1 µm; between about 50 nm and about 5 µm; between about 50 nm and about 1 µm; between about 45 nm and about 5 µm; between about 45 nm and about 1 µm; between about 40 nm and about 5 µm; between about 40 nm and about 1 µm; between about 35 nm and about 5 µm; between about 35 nm and about 1 µm; between about 30 nm and about 5 µm; between about 30 nm and about 1 µm; between about 25 nm and about 5 µm; between about 25 nm and about 1 µm; between about 20 nm and about 5 µm; between about 20 nm and about 1 µm, e.g., about 25, 30, 35, 40, 45, 50, 55, 60, 65, 70, 75, 80, 85, 90, 95, 100, 110, 120, 130, 140, 150, 160, 170, 180, 190, 200, 210, 220, 230, 240, 250, 260, 270, 280, 290, 300, 310, 320, 33, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 900, 910, 920, 930, 940, 950, 960, 970, 980, 990, or about 1000 nm, or about 0.5, 1, 1.5, 2, 2.5, 3, 3.5, 4, 4.5, or about 5 microns thick.

Subsequent to disposing the fiber layer over the first surface of the support and over the adipocytes, the adipocytes may be cultured under suitable conditions (e.g., at 37° C.) until at least some of the adipocytes grow to a diameter of between about 50 μm and about 280 μm; between about 80 μm and about 280 μm; between about 90 μm and about 280 μm; or between about 130 μm and about 280 μm. Expression of adipocyte markers including adiponectin, leptin, Peroxisome Proliferator Activated Receptor gamma 2 (PPARG2) and CCAAT/enhancer-binding protein (C/EBP) alpha, etc. can also be used to inform timing of disposing the fiber layer. The timing of disposing the fiber layer can also be guided by requirements for co-cultured cell types for example endothelial cells and/or vasculature, neurons and/or nerves, stromal cells and/or fibroblasts and/or preadipocytes and/or pericytes, and/or other components of the adipocyte niche.

In one embodiment, the mature adipocytes maintain their viability and functionality for at least 20 days, at least 22 days, at least 24 days, at least 26 days, at least 28 days, at least 30 days, at least 31 days, at least 32 days, at least 33 days, at least 34 days, at least 35 days, at least 36 days, at least 37 days, at least 38 days, at least 39 days, at least 40 days, at least 41 days, at least 42 days, at least 43 days, at least 44 days, at least 45 days, at least 46 days, at least 47 days, at least 48 days, at least 49 days, at least 50 days, at least 51 days, at least 52 days, at least 53 days, at least 54 days, at least 55 days, at least 56 days, at least 57 days, at least 58 days, at least 3590 days, at least 60 days or more.

The present invention also provides methods for making a support system for producing mature adipocytes in vitro. The methods include providing a support, such as a support described above; forming or depositing a pattern of islands on a first surface of the support (e.g., by microcontact printing), each island having a length, width, or diameter in a range of about 10 μm to about 100 μm (e.g., about 10 μm to about 60 μm; about 20 μm to about 50 μm; or about 20 μm to about 40 μm), and a center to center spacing between adjacent islands being in a range of about 20 μm to about 300 μm, each island comprising one or more layers of an extracellular matrix protein (e.g., fibronectin); and providing a fiber layer dimensioned to cover the pattern of islands on the first surface of the support after the islands are seeded with mesenchymal progenitor cells, the fiber layer comprising a plurality of polymer fibers each having a diameter in a range of about 100 nm to about 1 μm, e.g., about 400 nm to about 800 nm; or
about 420 to about 620 nm.

In one embodiment, providing the fiber layer dimensioned to cover the pattern of islands on the first surface of the support after the islands are seeded with mesenchymal progenitor cells includes forming the polymeric fibers by rotary jet spinning a polymer or pull-spinning; and collecting the polymeric fibers on a surface forming a fiber layer.

The polymeric fibers may be collected on a surface of a frame; or the polymeric fibers may be collected on a surface of multiple frames connected to or attached to each other to and the collection of the fibers forms a large fiber layer; and wherein the method further comprises cutting out a layer of fibers corresponding to each frame from the large fiber layer.

In one embodiment, cutting out a layer of fibers corresponding to each frame from the large fiber layer also separates the multiple frames from each other.

Each of the polymer fibers may independently comprise great than about 50 wt % polycaprolactone (PCL); and about 5 to about 49 wt % gelatin.

The present invention also provides a plurality of mature adipocytes produced according to any of the methods herein, as well as a tissue-engineered food product comprising a plurality of the mature adipocytes produced according to any of the methods herein.

III. Uses of the Mature Adipocytes of the Invention

The methods for producing mature adipocytes and the mature adipocytes produced according to the methods of the invention are suitable for use in, among other things, forming engineered tissue. Such tissue is useful not only for the production of prosthetic devices and regenerative medicine, but also for investigating tissue developmental biology and disease pathology, as well as in drug discovery and toxicity testing. The mature adipocytes produced according to the methods of the invention may also be combined with other substances, such as, therapeutic agents, in order to deliver such substances to the site of application or implantation of the mature adipocytes produced.

In some embodiments, methods for producing mature adipocytes and the mature adipocytes produced according to the methods of the invention are used for the culture of three-dimensional tissues in tissue engineering application as, e.g., synthetic adipose tissue. For example, a three-dimensional scaffold or plurality of three-dimensional scaffolds of the invention may be implanted or grafted in a subject, using standard surgical techniques.

Accordingly, the present invention provides methods of treating a subject needing reconstructive or cosmetic surgery. The methods include providing the mature adipocytes of the invention and implanting the mature adipocytes in the subject.

In some embodiments, the mature adipocytes of the invention may be combined with engineered muscle tissue products to produce engineered meat having the consistency of natural meat.

The mature adipocytes of the invention are also useful for screening compounds that modulate a property of the cells contained therein. The methods include providing a mature adipocyte prepared according to the methods of the invention; contacting the cell with a test compound; and monitoring a parameter in the absence of the compound (negative control) and in the presence of the compound; wherein a change in the parameter in the presence of the test compound compared to the parameter in absence of the test compound indicates that the test compound is effective in modulating the property.

In one embodiment, the parameter is growth, division, differentiation, or viability of the adipocytes.

Identification of a test compound that modulates the cell property may also be made by evaluating various physiological parameters such as cell morphology, cell structure, cell agglutination, formation of cell clusters, cell size, presence or absence of vesicles/granules, etc. In some embodiments, the assays may include measuring cellular uptake of labeled sugars, cellular assimilation of glycogen, etc. In other instances, the assays may include analyzing adipose-specific enzymes, e.g., hormone-sensitive lipase activity. Such techniques and methods are known in the art.

In one aspect, the present invention provides a method for identifying a compound that modulates adipocyte viability, adipocyte hypertrophy, and/or adipocyte function. The methods include providing a support having a first surface including a pattern of islands, each island having a length, width, or diameter in a range of about 10 μm to about 100 μm, and a center to center spacing between adjacent islands being in a range of about 20 μm to about 300 μm, each island comprising one or more layers of an extracellular matrix protein; seeding the pattern of islands with a plurality of mesenchymal progenitor cells and culturing the mesenchymal progenitor cells under conditions that induce adipogenesis of at least one of the mesenchymal progenitor cells, thereby producing adipocyte islands; contacting the adipocyte islands with a test compound; disposing a fiber layer over the first surface of the support and over the adipocytes on the islands, each fiber layer comprising a plurality of polymer fibers each having a diameter in a range of about 100 nm to about 1 μm; culturing the adipocytes with the fiber layer over the adipocytes under suitable conditions until at least one of the adipocytes grows to a diameter of between about 20 μm and about 300 μm; and determining the effect of the test compound on adipocyte viability, adipocyte hypertrophy, and/or adipocyte function in the presence and absence of the test compound, wherein a modulation of adipocyte viability, adipocyte hypertrophy, and/or adipocyte function in the presence of said test compound as compared to adipocyte viability, adipocyte hypertrophy, and/or adipocyte function in the absence of said test compound indicates that said test compound modulates adipocyte viability, adipocyte hypertrophy, and/or adipocyte function, thereby identifying a compound that modulates adipocyte viability, adipocyte hypertrophy, and/or adipocyte function.

In another aspect, the present invention provides a method for identifying a compound that modulates adipocyte viability, adipocyte hypertrophy, and/or adipocyte function. The methods include providing a support having a first surface including a pattern of islands, each island having a length, width, or diameter in a range of about 10 μm to about 100 μm, and a center to center spacing between adjacent islands being in a range of about 20 μm to about 300 μm, each island comprising one or more layers of an extracellular matrix protein; seeding the pattern of islands with a plurality of mesenchymal progenitor cells and culturing the mesenchymal progenitor cells under conditions that induce adipogenesis of at least one of the mesenchymal progenitor cells, thereby producing adipocyte islands; disposing a fiber layer over the first surface of the support and over the adipocytes on the islands, each fiber layer comprising a plurality of polymer fibers each having a diameter in a range of about 100 nm to about 1 μm; culturing the adipocytes with the fiber layer over the adipocytes under suitable conditions until at least one of the adipocytes grows to a diameter of between about 30 μm and about 300 μm; contacting the adipocyte with a test compound; and determining the effect of the test compound on adipocyte viability, adipocyte hypertrophy, and/or adipocyte function in the presence and absence of the test compound, wherein a modulation of adipocyte viability, adipocyte hypertrophy, and/or adipocyte function in the presence of said test compound as compared to adipocyte viability, adipocyte hypertrophy, and/or adipocyte function in the absence of said test compound indicates that said test compound modulates adipocyte viability, adipocyte hypertrophy, and/or adipocyte function, thereby identifying a compound that modulates adipocyte viability, adipocyte hypertrophy, and/or adipocyte function.

As used herein, the various forms of the term "modulate" are intended to include stimulation (e.g., increasing or upregulating a particular response or activity) and inhibition (e.g., decreasing or downregulating a particular response or activity).

As used herein, the term "contacting" (e.g., contacting a mature adipocyte with a test compound) is intended to include any form of interaction (e.g., direct or indirect interaction) of a test compound and cells. The term contacting includes incubating a compound and cell together (e.g., adding the test compound to a cell culture comprising mature adipocytes in culture).

Test compounds, may be any agents including chemical agents (such as toxins), small molecules, pharmaceuticals, peptides, proteins (such as antibodies, cytokines, enzymes, and the like), nanoparticles, and nucleic acids, including gene medicines and introduced genes, which may encode therapeutic agents, such as proteins, antisense agents (i.e., nucleic acids comprising a sequence complementary to a target RNA expressed in a target cell type, such as RNAi or siRNA), ribozymes, and the like.

The test compound may be added by any suitable means. For example, the test compound may be added drop-wise onto the surface of the cells and allowed to diffuse into or otherwise enter the device, or it can be added to the nutrient medium and allowed to diffuse through the medium. In the embodiment, where the support comprises a multi-well plate, each of the culture wells may be contacted with a different test compound or the same test compound. In one embodiment, the screening platform includes a microfluidics handling system to deliver a test compound and simulate exposure of the microvasculature to drug delivery.

IV. Kits of the Invention

The present invention also provides kits for producing mature adipocytes. The kits may include a support having a first surface including a pattern of islands, each island having a length, width or diameter in a range of about 10 μm to about 100 μm, and a center to center spacing between adjacent islands being in a range of about 20 μm to about 300 μm, each island comprising one or more layers of a matrix protein, and each island configured to support culture of mesenchymal progenitor cells through adipogenesis of at least one of the mesenchymal progenitor cells to produce adipocytes on the islands; and a fiber layer configured to be disposed over the first surface of the support and over the cells after adipogenesis of at least one of the cells, the fiber layer comprising a plurality of polymer fibers each having a diameter in a range of about 100 nm to about 1 μm; wherein the support and the fiber layer are configured to support maturation and/or hypertrophy of the adipocytes in culture up to a diameter of between about 30 μm and about 300 μm.

Each island may have a length, width, or diameter in a range of about 10 μm to about 60 μm; about 20 μm to about 50 μm; or about 20 μm to about 40 μm. Ranges and values intermediate to the foregoing are also included in the present invention.

In one embodiment, the polymer fibers of the fiber layer each independently comprise greater than about 50 wt % polycaprolactone (PCL); and about 5 to about 49 wt % gelatin.

Each of the polymer fibers may independently have a diameter in a range of about 400 nm to about 800 nm; or about 420 nm to about 620 nm.

The fiber layer may be attached to a frame having an outer diameter similar to that of a well of a culture plate; and the support may disposed in a well of a culture plate or the support is at least a portion of a bottom surface of the well of the culture plate.

In some embodiments, the kits of the invention further comprise one or more additional supports. Each support may have a first surface with a pattern of islands; and one or more additional fiber layers, each fiber layer attached to a corresponding frame, wherein the one or more additional supports are each disposed in a corresponding well of the culture plate or each of the one or more additional supports is at least a portion of a bottom surface of the corresponding well of the culture plate.

The kit may be specifically for culturing adipocytes to a selected final diameter, and wherein a center to center spacing of the islands corresponds to the selected desired final diameter of the adipocytes.

Suitable supports, polymers, methods for patterning the islands etc. are described above.

The practice of the presently disclosed subject matter can employ, unless otherwise indicated, conventional techniques of cell biology, cell culture, molecular biology, transgenic biology, microbiology, recombinant DNA, and immunology, which are within the skill of the art. Such techniques are explained fully in the literature. See e.g., *Molecular Cloning A Laboratory Manual* (1989), 2nd Ed., ed. by Sambrook, Fritsch and Maniatis, eds., Cold Spring Harbor Laboratory Press, Chapters 16 and 17; U.S. Pat. No. 4,683,195; *DNA Cloning, Volumes I and II*, Glover, ed., 1985; Oligonucleotide Synthesis, M. J. Gait, ed., 1984; *Nucleic Acid Hybridization*, D. Hames & S. J. Higgins, eds., 1984; *Transcription and Translation*, B. D. Hames & S. J. Higgins, eds., 1984; *Culture Of Animal Cells*, R. I. Freshney, Alan R. Liss, Inc., 1987; *Immobilized Cells And Enzymes*, IRL Press, 1986; Perbal (1984), *A Practical Guide To Molecular Cloning*; See Methods In Enzymology (Academic Press, Inc., N.Y.); *Gene Transfer Vectors For Mammalian Cells*, J. H. Miller and M. P. Calos, eds., Cold Spring Harbor Laboratory, 1987; *Methods In Enzymology*, Vols. 154 and 155, Wu et al., eds., Academic Press Inc., N.Y.; *Immunochemical Methods In Cell And Molecular Biology* (Mayer and Walker, eds., Academic Press, London, 1987; *Handbook Of Experimental Immunology*, Volumes I-IV, D. M. Weir and C. C. Blackwell, eds., 1986.

The entire contents of all references, patents and published patent applications cited throughout this application, as well as the Figures, are hereby incorporated herein by reference.

We claim:

1. A method for producing one or more mature adipocytes in vitro, comprising;
    seeding a plurality of mesenchymal progenitor cells into a seeding site;
    culturing the mesenchymal progenitor cells under conditions that induce adipogenesis of one or more of the mesenchymal progenitor cells, thereby producing one or more adipocytes;
    disposing a fiber layer over the one or more adipocytes, the fiber layer comprising a plurality of polymer fibers each having a diameter in a range of about 100 nm to about 1 µm; and
    culturing the one or more adipocytes with the fiber layer over the one or more adipocytes under suitable conditions until each of the one or more adipocytes grows to a diameter of between about 30 µm and about 300 µm, thereby generating one or more mature adipocytes in vitro.

2. The method of claim 1, wherein the one or more adipocytes are cultured with the fiber layer over the one or more adipocytes until at least one of the one or more adipocytes grows to a diameter of between about 50 µm and about 280 µm.

3. The method of claim 1, wherein each of the polymer fibers comprises greater than about 50 wt % polycaprolactone (PCL).

4. The method of claim 3, wherein each of the polymer fibers further comprises about 5 to about 49 wt % gelatin.

5. The method of claim 1, wherein each of the polymer fibers has a diameter in a range of about 400 nm to about 800 nm.

6. The method of claim 1, further comprising:
    providing a support having a first surface including a pattern of islands, each island having a length, width, or diameter in a range of about 10 µm to about 100 µm, and a center to center spacing between adjacent islands being in a range of about 20 µm to about 300 µm, each island comprising one or more layers of an extracellular matrix protein.

7. The method of claim 6, wherein the seeding site includes the pattern of islands.

8. The method of claim 6, wherein the spacing between the islands is a function of cell seeding density.

9. The method of claim 6, wherein the islands are formed via micropatterning.

10. The method of claim 6, wherein each island has a length, width, or diameter in a range of about 10 µm to about 60 µm.

11. The method of claim 1, wherein the mesenchymal progenitor cells are derived from pre-adipocytes.

12. The method of claim 1, wherein the mesenchymal progenitor cells are derived from pluripotent stem cells.

13. The method of claim 1, further comprising:
    differentiating at least a portion of the mesenchymal progenitor cells into at least one of osteoblasts, chondrocytes, fibroblast, preadipocytes, pericytes, or myocytes.

14. The method of claim 1, wherein the fibers include at least one of proteins, polysaccharides, lipids, or nucleic acids.

15. The method of claim 1, wherein the mesenchymal progenitor cells are seeded into a scaffold.

16. The method of claim 1, wherein each of the polymer fibers has a diameter in a range of about 420 nm to about 620 nm.

17. A method for producing a tissue-engineered food product, the method comprising:
    seeding a plurality of mesenchymal progenitor cells into a seeding site;
    culturing the mesenchymal progenitor cells under conditions that induce adipogenesis of one or more of the mesenchymal progenitor cells, thereby producing one or more adipocytes;
    disposing a fiber layer over the one or more adipocytes, the fiber layer comprising a plurality of polymer fibers each having a diameter in a range of about 100 nm to about 1 µm;
    culturing the one or more adipocytes with the fiber layer over the one or more adipocytes under suitable conditions until each of the one or more adipocytes grows to a diameter of between about 30 µm and about 300 µm, thereby generating one or more mature adipocytes; and combining the one or more mature adipocytes with an engineered muscle tissue product to produce an engineered meat, thereby producing a tissue-engineered food product.

* * * * *